US008246965B2

(12) United States Patent
Jacobsen et al.

(10) Patent No.: US 8,246,965 B2
(45) Date of Patent: Aug. 21, 2012

(54) *BACILLUS* ISOLATES AND METHODS OF THEIR USE TO PROTECT AGAINST PLANT PATHOGENS

(75) Inventors: Barry Jacobsen, Bozeman, MT (US); Nina K. Zidack, Bozeman, MT (US); Rebecca Larson, Longmont, CO (US)

(73) Assignee: Montana State University, Bozeman, MT (US)

( * ) Notice: Subject to any disclaimer, the term of this patent is extended or adjusted under 35 U.S.C. 154(b) by 0 days.

(21) Appl. No.: 13/204,315

(22) Filed: Aug. 5, 2011

(65) Prior Publication Data

US 2011/0318386 A1    Dec. 29, 2011

Related U.S. Application Data

(63) Continuation of application No. 12/557,975, filed on Sep. 11, 2009, now Pat. No. 8,025,875, which is a continuation-in-part of application No. 11/361,283, filed on Feb. 24, 2006, now abandoned.

(51) Int. Cl.
*A61K 39/07*    (2006.01)
*C12N 1/20*    (2006.01)

(52) U.S. Cl. .................................. 424/246.1; 435/252.5

(58) Field of Classification Search .................. None
See application file for complete search history.

(56) References Cited

U.S. PATENT DOCUMENTS

| 6,031,153 A * | 2/2000 | Ryals et al. ..................... 800/279 |
| 2006/0029576 A1 * | 2/2006 | Huang et al. .................. 424/93.4 |
| 2007/0224179 A1 | 9/2007 | Jacobsen et al. |
| 2010/0092442 A1 * | 4/2010 | Jacobsen et al. ........... 424/93.46 |

OTHER PUBLICATIONS

Zaitlin et al. (Annual Review in Phytopathology. 2000; 38: 117-143).*
Chen et al. (European Journal of Plant Pathology. 2009; 124: 427-437).*
Enya et al. (Microbial Ecology. 2007; 53:524-536).*
Haye et al. (Proceedings of the Third International Symposium on Biological Control of Arthrpods. 2008: 403-415).*
Matsuda et al. (Journal of Agricultural Food Chemistry. 1998; 46: 4416-4419).*
Garbelotto et al. (Plant Pathology. 2008; Doi: 10.1111/j.1365-3059. 2008.01894: 1-9).*
Cheng et al. (Journal of Agricultural Research in China. 1988; 37 (3): 320-327).*
Gust et al. (Current Opinion in Biotechnology. 2010; 21: 204-210).*
Bargabus et al. (Physiological and Molecular Plant Pathology. 2002; 61: 289-298).*
Barbagus et al. (Biological Control. 2004; 30: 342-350).*
Jacobsen et al., "Integrated Management of *Cercospora* Leaf Spot", Jan. 1998, 1997 Sugarbeet Research and Extension Reports, vol. 28, pp. 317-320.

Jacobsen et al., "Fungicide and Biological Control Alternatives to TPTII for *Cercospora* Leaf Spot Control", Jan. 1999, 1998 Sugarbeet Research and Extension Reports, vol. 29, pp. 350-356.
Jacobsen et al., "*Cercospora* Leaf Spot Control Research at Sidney, MT IN 1998", Jan. 2000, 1999 Sugarbeet Research and Extension Reports, vol. 30, pp. 287-288.
Jacobsen et al., "Management of *Cercospora* Leaf Sport in Western North Dakota and Eastern Montana", Jan. 2001, 2000 Sugarbeet and Extension Reports, vol. 31, pp. 273-276.
Jacobsen et al., "Integration of *Bacillus* sp. biological seed treatments with apron-thiram and apron-thiram-tachigaren seed treatments for biological control of pythium and aphanomyces seedling diseases", and "Integrated Managment strategies for *Rhizoetonia crown* and Root Rot", Jan. 2002, 2001 Sugarbeet Research and Extension Reports, vol. 32, pp. 262-265.
Alvarez et al., "Reactive Oxygen Intermediates Mediate a Systemic Signal Network in the Establishment of Plant Immunity", *Cell*, 92:773-784, Mar. 20, 1998.
Kloepper et al., "Induced Systemic Resistance and Promotion of Plant Growth by *Bacillus ssp.*", 2004. Phytopathology. 94:1259-1266.
Alström, S., "Induction of Disease Resistance in Common Bean Susceptible to Halo Blight Bacterial Pathogen After Seed Bacterisation With *Rhizosphere pseudomonads*," Journal of Genetic and Applied Microbiology, 37:495-50 1 (1991), USA.
Andrews, J.H., "Biological Control in The Phyllosphere," Annual Review of *Phytopathology*, 30:603-635 (1992), USA.
Bargabus, R.L., et al., "Oxidative Burst Elicited by *Bacillus mycoides* Isolate Bac J, a Biological Control Agent, Occurs Independently of Hypersensitive Cell Death in Sugar Beet," American Phytopathological Society vol. 16, No. 12, 2003, pp. 1145-1153, USA.
Bargabus, R.L., et al., "*Bacillus mycoides* Isolate Bac J Elicits an Oxidative Burst Independent of Hypersensitive Cell Death," APS Abstracts of Presentations (2003) APS Annual Meeting, Aug. 9-13, 2003, Charlotte, Nc, USA.
Bargabus, R.L., et al., "Elicitation of ISR by a Nonpathogenic Phyllosphere Inhabiting Bacterium," APS Annual Meeting, Aug. 25-29, 2001 Poster Abstract, Charlotte, NC, USA.
Bargabus, R.L., et al., "Host-response Based Screening of Biological Control Agents," APS Abstracts of Presentations (2002) APS Annual Meeting, Jul. 27-31, 2002, Midwest Express Center, Milwaukee, Wisconsin, USA.
Bargabus-Larson, R.L., et al., "Biocontrol Elicited Systemic Resistance in Sugarbeet is Salicylic Acid Independent and NPRI Dependent," USDA, Agricultural Research Service, Sugarbeet Research Unit, 1701 Centre Avenue, Fort Collins, Colorado and Montana State University, Biocontrol Elicited Systemic Resistance, pp. 17-33, Jan.-Jun. 2007, USA.
Doke, N., "Generation of Superoxide Anion by Potato Tuber Protoplasts During The Hypersensitive Response to Hyphal Wall Components of Phytophthora Infestans and Specific Inhibition of the Reaction by Suppressors of Hypersensitivity," Physiological Plant Patholom, 23:359-367 (1983), USA.

(Continued)

*Primary Examiner* — Shanon A Foley
(74) *Attorney, Agent, or Firm* — Cooley LLP

(57) ABSTRACT

*Bacillus* isolates and compositions comprising the same are provided. Also provided are methods of inducing systemic acquired resistance to infection in a plant by applying a composition comprising a *Bacillus* control agent to said plant wherein said plant is capable of producing defense proteins.

16 Claims, 4 Drawing Sheets

OTHER PUBLICATIONS

Jacobsen, B.J., et al., "The Role of *Bacillus*-based Biological Control Agents in Integrated Pest Management Systems," Abstracts of Special Session Presentations APS Annual Meeting Aug. 9-13, 2003, Charlotte, NC, USA.

Jacobsen, B.J., el al., "Commericalization of *Bacillus mycoides* Isolate BmJ as a Broad Spectrum Biological Plant Disease Control Agent," Phytopathology 97:S50, USA, 2007.

Johnson, C., et al., "Salicylic Acid and NPRI Induce the Reqruitment of Trans-Activating TGA Factors to a Defense Gene Promoter in *Arabidopsis*," The Plant Cell, vol. 15, 1846-1858 (2003), USA.

Kuc, J., "Induced Immunity to Plant Disease," BioScience, 32:854-860 (1982), USA.

Larson, B.J., et al., "Integrating Fungicides and a *Bacillus mycoides* Biological Control Agent to Manage *Cercospora* Leaf Spot Resistance to Fungicides," APS Abstracts of Presentations, APS 2002 Annual Meeting, Jul. 27-31, 2002, Midwest Express Center, Milwaukee, Wisconsin, USA.
Neher, O.T., et al., "Control of Anthracnose of Cucurbits Caulsed by *Glomerella cingulata* Var. Orbiculare by Foliar Applications of *Bacillus mycoides*, Isolate BmJ," Phytopathology 97: S83, USA.
Pieterse, C.M.J., el al., "Systemic Resistance in *Arabidopsis* Induced by Biocontrol Bacteria is Independent of Salicylic Acid Accumulation and Pathogenesis-related Gene Expression," The Plant Cell. 8:1225-1237 (1996), USA.
Sampson, M.N., et al., "Involvement of Chitinases of *Bacillus thuringiensis* During Pathogenesis in Insects," Microbiology, 144:2 189-2 194 (1998), USA.
Santos, et al., "In a Compatible Plant-pathogen Interaction, a Single, Rapid Burst of Hydrogen Peroxide is Observed," MPMI vol. 14, No. 1, 2001, pp. 86-89. Publication No. M-2000-1117-01N, The American Phytopathological Society (2001), USA.
Sequeira, L., "Mechanisms of Induced Resistance in Plants," Annual Review of Microbiology, 37:5, 1-79 (1983), USA.
Tally, A., el al., "Commercial Development of Elicitors of Induced Resistance to Pathogens," Induced Plant Defenses Against Pathogens and Herbivores (A.A. Agrawal, S. Tuzun, and E. Bent, eds.) St. Paul: APS Press, 357-369 (1999), USA.
Wei, G., et al., "Induction of Systemic Resistance of Cucumber to *Colletotrichum orbiculare* by Select Strains of Plant Growth-promoting *Rhizobacteria*," Phytopathology, 81:1508-1512 (1991), USA.
Zietlow, O.T., el al., "Induced Systemic Resistance in Cucumber to *Glomerella cingulata* Var. *Orbiculare* and *Pseudomans syringae* pv. *Lachrymans* by *Bacillus mycoides*, Isolate BacJ and *Bacillus pumilus*, Isolate MSU 203-7," APS Abstracts of Presentations, 2004 Annual Meeting of the American Phytological Society, USA.
Neher et al., "Defense pathways activated by *Bacillus mojavensis* isolate 203-7 and *B. mycoides* isolate BmJ as elucidated by *Arabidopsis*, mutants", Abstract of Presentations, Sep. 11, 2008, $X^{th}$ meeting of the working group, biological control of fungal and bacterial plant pathogens, International Organization for Biological and Integrated Control of Noxious Animals and Plants. Interlaken, Switzerland.

* cited by examiner

BACILLUS ISOLATES AND METHODS OF THEIR USE TO PROTECT AGAINST PLANT PATHOGENS

CROSS-REFERENCE TO RELATED APPLICATIONS

This application claims priority to, and is a continuation of U.S. patent application Ser. No. 12/557,975, filed on Sep. 11, 2009, now U.S. Pat. No. 8,025,875, which is a continuation-in-part of U.S. patent application Ser. No. 11/361,283, filed on Feb. 24, 2006, now abandoned. Each of the above applications is hereby incorporated by reference in its entirety for all purposes.

GOVERNMENT RIGHTS STATEMENT

This invention was made with government support under grant number 2001-35316-11109 awarded by USDA/CSREES. The government has certain rights in the invention.

FIELD OF THE INVENTION

This invention generally relates to methods of inducing pathogen resistance in plants, such as inducing systemic acquired resistance to infection in plants. In one aspect, this invention relates to methods of inducing systemic acquired resistance to infection in plants comprising applying a *Bacillus* control agent comprising *Bacillus mojavensis* isolate 203-7 and/or *Bacillus mycoides* isolate BmJ to one or more plants.

BACKGROUND OF THE INVENTION

Effective biological control of plant diseases with epiphytic microbes has been documented for numerous phyllosphere- and rhizosphere-inhabiting organisms. Foliar biological control agents include yeast and filamentous fungi (see Hofstein R and A. Chapple, "Commercial development of biofungicides," Biopesticides: Use and Delivery (Hall F R, Menn J J, eds.), Totowa: Humana Press (1999); and Sutton, J. C. and G. Peng, "Manipulation and vectoring of biocontrol organisms to manage foliage and fruit diseases in cropping systems," Annual Review of Phytopathology, 31:473-493 (1993)) as well as bacteria; including both gram (−) species such as *Erwinia* sp. and *Pseudomonas* sp. (see Andrews, J. H., "Biological control in the phyllosphere," Annual Review of Phytopathology, 30:603-635 (1992)), and gram (+) organisms such as *Bacillus* sp. See Kokalis-Burelle, N., P. A. Backman, R Rodriquez-Kabana, and L. D. Ploper, "Potential for biological control of early leafspot of peanut using *Bacillus cereus* and chitin as foliar amendments," Biological Control, 2:321-328 (1992). Biological control agents applied to the rhizosphere include Pseudomonads (see Alstrom, S., "Induction of disease resistance in common bean susceptible to halo blight bacterial pathogen after seed bacterisation with rhizosphere pseudomonads," Journal of Genetic and Applied Microbiology, 37:495-501 (1991); van Peer, R, G. J. Niemann, and B. Schippers, "Induced resistance and phytoalexin accumulation in biological control of *fusarium* wilt of carnation by *Pseudomonasa* sp. strain WCS417r," Phytopathology, 81:728-734 (1991); and van Loon L. C. and C. M. J. Pieterse, "Biological control agents in signaling resistance," Biological Control of Crop Diseases (Gnanamanickan SS, ed.), New York: Mercel Dekker, Inc. 486 (2002)) as well as *Bacillus* sp. (see Zhang, S., M. S. Reddy, N. Kokalis-Burelle, L. W. Wells, S. P. Nightengale, and J. W. Kloepper, "Lack of induced systemic resistance in peanut to late leaf spot disease by plant growth-promoting rhizobacteria and chemical elicitors," Plant Disease, 85(8):879-884 (2001); and Murphy, J. F., G. W. Zehnder, D. J. Schuster, E. J. Sikora, J. E. Polston, and J. W. Kloepper, "Plant growth-promoting rhizobacterial mediated protection in tomato against Tomato mottle virus," Plant Disease, 84(7):779-784 (2000)) that are classically referred to as plant growth-promoting rhizobacteria. For the most part biological disease control is attributed to direct antagonism against the pathogen via production of antibiotics or hydrolytic enzymes, or through competition for nutrients. See Weller. D. M., "Biological control of soil-borne plant pathogens in the rhizosphere with bacteria." Annual Review of Phytopathology. 26:379-407 (1988). However, plant growth-promoting rhizobacteria and rhizosphere inhabiting fungi have been shown to stimulate the induction of systemic resistance responses within the plant. See van Peer. R. G. J. Niemann. and B. Schippers, "Induced resistance and phytoalexin accumulation in biological control of fusarium wilt of carnation by *Pseudomonasa* sp. strain WCS417r." Phytopathology, 81:728-734.(1991); Wei. G. J. W. Kloepper, and S. Tuzun, "Induction of systemic resistance of cucumber to *Colletotrichum orbiculare* by select strains of plant growth-promoting rhizobacteria," Phytopathology, 81:1508-1512 (1991); van Loon, L. C. and C. M. J. Pieterse, "Biological control agents in signaling resistance." Biological Control of Crop Diseases (Gnanamanickan. S. S., ed.). New York: Mercel Dekker, Inc. 486 (2002). All publications mentioned above are incorporated herein by reference in their entireties for all purposes.

Systemic induced resistance (SIR) has been described in many plant systems, most notably tobacco, bean, tomato, cucumber, and *Arabidopsis thaliana*. See Ross, A F., "Localized acquired resistance to plant virus infection in hypersensitive hosts," Virology, 14:329-339 (1961); Kuc, J., "Induced immunity to plant disease," BioScience, 32:854-860 (1982); Ryals, J. A., U. H. Neuenschwander, M. G. Willits, A. Molina, H. Y. Steiner, and M. D. Hunt, "Systemic acquired resistance," The Plant Cell. 8:1809-1819 (1996); and van Loon, L. C. and C. M. J. Pieterse, "Biological control agents in signaling resistance." Biological Control of Crop Diseases (Gnanamanickan. S. S., ed.). New York: Mercel Dekker, Inc. 486 (2002). The broad-spectrum resistance makes an otherwise susceptible plant resistant to a wide array of subsequent pathogen attacks. See Kuc, J. "Induced immunity to plant disease," BioScience, 32:854-860 (1982); and Hutcheson, S. W., "Current concepts of 'active defense in plants." Annual Review of Phytopathology, 36:59-90 (1998). Elicitation of systemic disease resistance in plants has thus far been achieved through treatment by three types of stimuli: necrotizing pathogens (see Pieterse, C. M. J., S. C. M. van Wees. E. Hoffland, J. A. van Pelt, and L. C. van Loon, "Systemic resistance in *Arabidopsis* induced by biocontrol bacteria is independent of salicylic acid accumulation and pathogenesis-related gene expression," The Plant Cell, 8:1225-1237 (1996); Ross, AF., "Localized acquired resistance to plant virus infection in hypersensitive hosts,"Virology, 14:329-339 (1961); Ross. AF., "Systemic acquired resistance induced by localized virus infection in plants," Virology. 14:340-358 (1961); and Kuc, J., "Induced immunity to plant disease." BioScience. 32:854-860 (1982)), secondary signal molecules (Le. salicylic acid, SA) (see White, R. F., "Acetylsalicylic acid (aspirin) induces resistance to tobacco mosaic virus in tobacco," Virology. 99:410-412 (1979)) and their functional analogs (e.g. 2,6 dichloroisonicotinic acid, INA (see Metraux, J. P., P. Ahl-Goy, T. Staub, J. Speich, A Steinemann, J. Ryals, and E. Ward, "Induced resistance in cucumber in response to 2,6-dichloroisonicotinic acid and pathogens," Advances in Molecular Genetics of Plant-Microbe Interactions, Vol. 1. (H. Hennecke, D. P. S. Verma, eds.), Dordrecht: Kluwer Academic Publishers, 432-439 (1991)) and acibenzolar-5-methyl. ASM (see Tally, A, M. Oostendorp, K. Lawton, T. Staub, and B. Bassi, "Commercial development of elicitors of induced resistance to pathogens," Induced Plant Defenses Against Pathogens and Herbivores (A A Agrawal, S. Tuzun, and E. Bent, eds.) St. Paul: APS Press, 299-318 (1999)), and plant growth-promoting rhizobacteria introduction into the rhizosphere. See Alstrom, S., "Induction of disease resistance in common bean susceptible to halo blight bacterial pathogen after seed bacterisation with rhizosphere pseudomonads," Journal of Genetic and Applied Microbiology, 37:495-501 (1991); van Loon, L. C. and C. M. J. Pieterse, "Biological control agents in signaling resistance," Biological Control of Crop Diseases (Gnanamanickan, S. S., ed.), New York: Mercel Dekker, Inc, 486 (2002); Wei, G., J. W. Kloepper, and S. Tuzun, "Induction of systemic resistance of cucumber to *Colletotrichum orbiculare* by select strains of plant growth-promoting rhizobacteria," Phytopathology, 81:1508-1512 (1991); Zhang, S., M. S. Reddy, N. Kokalis-Burelle, L. W. Wells, S. P. Nightengale, and J. W. Kloepper, "Lack of induced systemic resistance in peanut to late leaf spot disease by plant growth-promoting rhizobacteria and chemical elicitors," Plant Disease, 85(8):879-884 (2001); and Murphy, J. F., G. W. Zehnder, D. J. Schuster, E. J. Sikora, J. E. Polston, and J. W. Kloepper, "Plant growth-promoting rhizobacterial mediated protection in tomato against Tomato mottle virus," Plant Disease, 84(7):779-784 (2000). Additionally, oomycete and fungal hyphal wall fragments (see Doke, N., "Generation of superoxide anion by potato tuber protoplasts during the hypersensitive response to hyphal wall components of *Phytophthora infestans* and specific inhibition of the reaction by suppressors of hypersensitivity," Physiological Plant Pathology, 23:359-367 (1983); and Anderson, A. J., "Studies on the structure and elicitor activity of fungal glucans," Canadian Journal of Botany, 58:2343-2348 (1980)), bacterial cell wall fractions (lipopolysaccharides) (see Sequeira, L., "Mechanisms of induced resistance in plants," Annual Review of Microbiology, 37:51-79 (1983), and phytohormones (see Cohen, Y., M. Reuveni, and A. Baider, "Local and systemic activity of BABA (DL-3-aminobutyric acid), against *Plasmopara viticola* in grapevines," European Journal of Plant Pathology, 105(4):351-361 (1999); Oka, Y., Y. Cohen, and Y. Spiegel, "Local and systemic induced resistance to the root-knot nematode in tomato by DL-beta-amino-n-butyric acid," Phytopathology, 89(12): 1138-1143 (1999); and Cohen, Y. R., "β-Aminobutyric acid-Induced Resistance Against Plant Pathogens," Plant Disease, 86(5):448-457 (2002)) have SIR-displayed induction capability. All publications mentioned above are incorporated herein by reference in their entireties for all purposes.

Two systemic resistance pathways have been described: 1) systemic acquired resistance, which utilizes salicylic acid as a secondary signal molecule and leads to the production of pathogenesis-related (PR) proteins (see Delaney, T. P., "Genetic Dissection of Acquired Resistance to Disease," Plant. Physiology, 113:5-12 (1997)) and 2) induced systemic resistance, which utilizes jasmonates and ethylene as secondary signal molecules and controls disease independently of PR-protein production (see Pieterse, C. M. J., S. C. M. van Wees, J. A. van Pelt, M. Knoester, R. Laan, H. Gerrits, P. J. Weisbeek, and L. C. van Loon, "A Novel Signaling Pathway Controlling Induced Systemic Resistance in *Arabidopsis*," The Plant Cell, 10:1571-1580 (1998)). All publications mentioned above are incorporated herein by reference in their entireties for all purposes.

Systemic resistance results in the activation of defenses in uninfected parts of the plant. As a result, the entire plant is more resistant to infection. The systemic resistance is long lasting and often confers broad-based resistance to different pathogens.

One of the issues surrounding systemic resistance is the occurrence of necrotic cell death at the site of application of the agent that induces systemic resistance.

Increased societal concerns related to the use of agrichemicals and genetically modified organisms as a means of managing crop diseases has prompted interest in methods of biological control. A biological control agent capable of inducing systemic resistance would provide a method of increasing disease resistance in a plant without the use of agrichemicals. Of particular interest would be a biological control agent capable of inducing systemic resistance without inducing necrotic cell death.

Thus, a need exists for new biological control agents capable of inducing systemic induced resistance in plants. A need also exists for new methods of identifying new biological control agents capable of inducing systemic resistance in plants.

SUMMARY OF THE INVENTION

In accordance with the objects outlined above, the present invention provides methods and compositions useful in inducing disease resistance to infection in a plant, comprising applying a *Bacillus* control agent comprising *Bacillus mojavensis* isolate 203-7 having accession number NRRL B-30893 and/or *Bacillus mycoides* isolate BmJ having accession number NRRL B-30890 to the plant, wherein the plant is capable of producing defense proteins. In one embodiment, the disease resistance to infection in the plant is systemic acquired resistance. In another embodiment, the systemic acquired resistance is induced in the plant through a salicylic acid independent and jasmonic acid dependent pathway. In another embodiment, the systemic acquired resistance is induced by *Bacillus mycoides* isolate BmJ having accession number NRRL B-30890 in the plant through an NPR1 dependent pathway. In another embodiment, the systemic acquired resistance is induced by *Bacillus mojavensis* isolate 203-7 having accession number NRRL B-30893 in the plant through an NON-EXPRESSOR OF PATHOGENESIS-RELATED GENES1 (NPR1) independent pathway. In another embodiment, the plant is a monocot, for example, the plant is selected from the group consisting of *Arabidopsis*, wheat, corn (maize), rice, barley, triticale and lily. In another embodiment, the plant is a dicot, for example, the plant is selected from the group consisting of banana, cucurbit, pecan, soybean, sunflower, alfalfa, tomato, cucumber, watermelon and geranium. In another embodiment, the infection is caused by any kind of infectious (i.e., biotic) agents that affect plants. Examples of such agents/pathogens include but are not limited to an agent or pathogen selected from the group consisting of bacteria, fungi, and viruses. Examples of specific pathogens to be treated using the compositions and methods of the present invention include but are not limited to pathogens selected from the group consisting of *Mycosphaerella tijiensis, Cladosporium caryigenum, Glomerella cingulata, Cercospora beticola, Pseudomonas syringe, Erwinia caratovora, Botrytis cinerea*, and *Fusarium solani* f. sp. *cucurbitae.*

The present invention also provides methods of inducing a first systemic acquired resistance in a plant comprising applying a *Bacillus* control agent comprising *Bacillus mojavensis* isolate 203-7 and/or *Bacillus mycoides* isolate BmJ to the plant, wherein the methods further comprise applying a second biological or chemical control agent, and wherein the first systemic acquired resistance is induced in the plant through a salicylic acid independent and jasmonic acid dependent pathway. In one embodiment, the first systemic acquired resistance is induced by *Bacillus mycoides* isolate BmJ having accession number NRRL B-30890 in the plant through an NPR1 dependent pathway. In another embodiment, the first systemic acquired resistance is induced by *Bacillus mojavensis* isolate 203-7 having accession number NRRL B-30893 in the plant through an NPR1 independent pathway. In another embodiment, the second biological or chemical control agent is selected from the group consisting of antifungal agents, antibacterial agents, antiviral agents, and plant activating compounds. The second biological or chemical control agent may or may not also induce the first systemic acquired resistance in the plant and/or induce a second systemic acquired resistance in the plant.

The invention is also directed to methods of screening for biological control agents useful in inducing systemic acquired resistance to infection in a plant.

The present invention, according to one embodiment, is a method of inducing systemic acquired resistance to infection in a plant. The method includes applying to the foliage of the plant a composition comprising a *Bacillus* control agent. The agent is *Bacillus mycoides* isolate BmJ having accession number NRRL B-30890 or *Bacillus mojavensis* isolate 203-7 having accession number NRRL B-30893. According to the invention, the plant is capable of producing defense proteins.

In an alternative embodiment, the present invention is a method of inducing systemic acquired resistance to infection in a plant. The method includes applying to the foliage of said plant a composition comprising a *Bacillus* control agent. The agent is *Bacillus mycoides* isolate BmJ having accession number NRRL B-30890 or *Bacillus mojavensis* isolate 203-7 having accession number NRRL B-30893. According to the invention, the plant does not experience necrotic cell death as a result of said applying of said *Bacillus* control agent.

According to one embodiment of the present invention, the infection to which systemic acquired resistance is induced is selected from the group consisting of bacterial infections, fungal infections, and viral infections. Alternatively, the infection is a *Mycosphaerella fijiensis* (Black sigatoka), *Cladosporium caryigenum* (pecan scab), *Glomerella cingulata* (Anthracnose) or *Cercospora beticola* (Cercospora leaf spot) infection. In a further alternative, the infection is a *Pseudomonas syringe* (angular leaf spot) or *Erwinia caratovora* (bacterial vascular necrosis) infection. In a further alternative, the infection is *Botrytis cinerea* or *Fusarium solani* f. sp. *cucurbitae* (Fusarium Crown rot).

In one aspect of the invention, either of the above methods also includes applying a biological or chemical control agent. According to one embodiment, the *Bacillus* biological control agent is applied in conjunction with the biological or chemical control agent. Alternatively, the *Bacillus* biological control agent is applied sequentially with the biological or chemical control agent.

The present invention, in accordance with another embodiment, is a plant treated with a *Bacillus* control agent selected from the group consisting of *Bacillus mycoides* isolate BmJ having accession number NRRL B-30890 and *Bacillus mojavensis* isolate 203-7 having accession number NRRL B-30893. The agent induces systemic acquired resistance in said plant. According to this embodiment, the plant does not experience necrotic cell death as a result of said treating with said *Bacillus* control agent and the plant is selected from the group consisting of a banana, a cucurbit, a pecan and a geranium plant.

According to another embodiment, the present invention is a method of screening for a *Bacillus* control agent that induces systemic resistance in a plant. The method includes contacting a plant sample with said *Bacillus* control agent and detecting a property selected from the group consisting of the release of active oxygen species (AOS), chitinase activity and $\beta$-1,3 glucanase activity.

In accordance with another aspect, the present invention is a composition for imparting systemic disease resistance in a plant capable of producing defense proteins. The composition includes a *Bacillus* control agent selected from the group consisting of *Bacillus mycoides* isolate BmJ having accession number NRRL B-30890 and *Bacillus mojavensis* isolate 203-7 having accession number NRRL B-30893. Further, the plant is capable of producing defense proteins. This composition can also alternatively include a carrier substance, a biological control agent, and/or a chemical control agent. According to one embodiment, the composition is a solution.

In another embodiment, the present invention is a method of inducing systemic acquired resistance to infection in a plant. The method includes causing the phyllosphere of the plant to be colonized with a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method is capable of producing defense proteins.

According to an alternative aspect, the present invention is a method of enhancing plant growth by conferring systemic acquired resistance to a plant. The method includes applying to the foliage of the plant a composition comprising a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method is capable of producing defense proteins.

The present invention, according to an alternative embodiment, is a method of enhancing plant growth by conferring systemic acquired resistance to a plant. The method includes causing the phyllosphere of the plant to be colonized with a composition comprising a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method is capable of producing defense proteins.

DETAILED DESCRIPTION OF THE INVENTION

Figure 1:
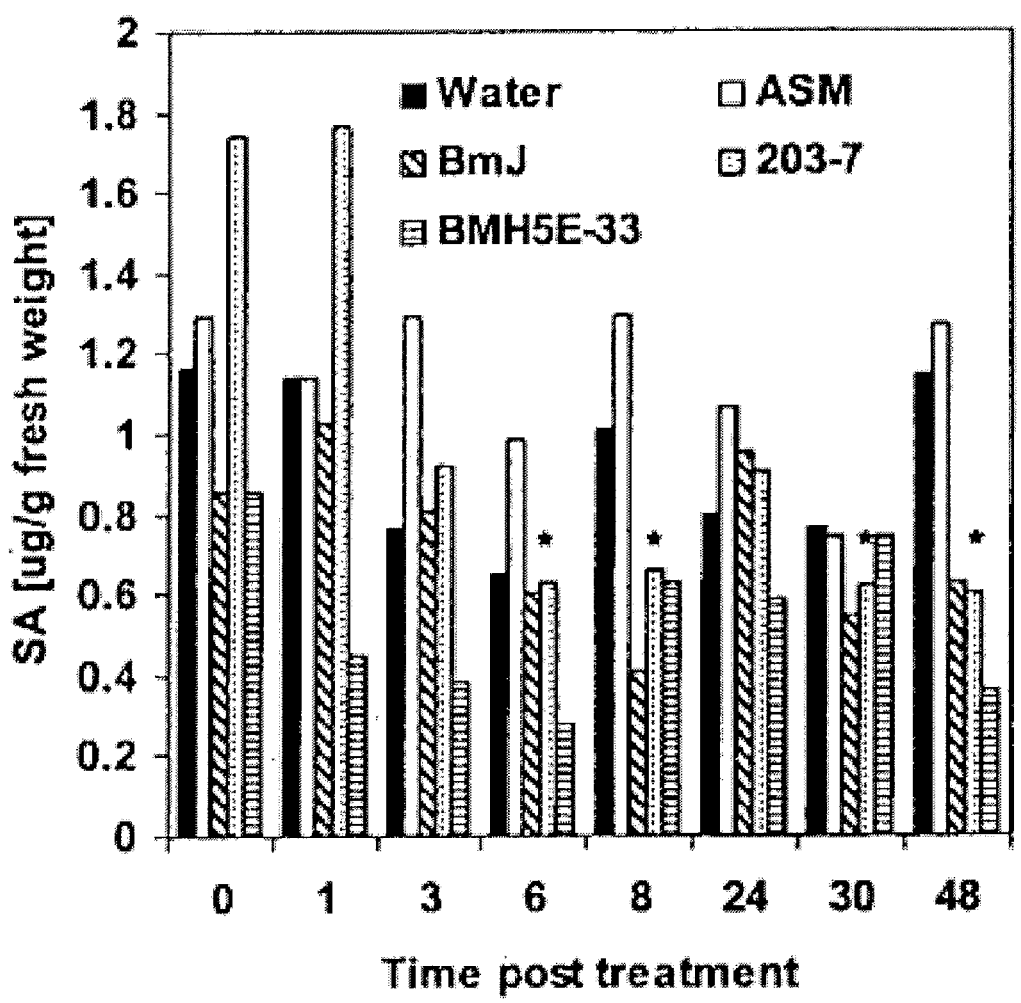
FIG. 1 depicts a graphic representation of the relationship between systemic resistance and accumulation of salicylic acid ("SA"), according to one embodiment of the present invention.

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, brassica leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other brassica leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of cucumis melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fibber crops (e.g. hemp, cotton), ornamentals, and the like. For a more complete list of representative crop plants see, for example, Glossary of Crop Science Terms: III, Nomenclature, Common and Scientific Names, Crop Science Society of America, July 1992, which is herein incorporated in its entirety.

As used herein, the term "pesticide" refers to composition comprising one or more chemical substances or biological organisms capable of killing or inhibiting a pest. Pests include, but are not limited to, insects, pathogens (e.g., bacterium, fungi, viruses), weeds, molluscs, birds, mammals, fish, nematodes and microbes that compete with humans, e.g., for food. Pesticides can be classified into algicides, avicides, bactericides, fungicides, herbicides, insecticides, miticides/acaricides, molluscicides, nematicides, rodenticides, virucides, et al.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots". For a more comprehensive list of plant parts see, for example, James W. Perry and David Morton (1998) Photo Atlas for Botany, Wadsworth Publishing Company, 141 pages, which is herein incorporated in its entirety.

As used herein, the term "fungicide" refers to a composition comprising one or more chemical substances or biological organisms capable of killing or inhibiting both true fungi and their spores as well as oomycete pathogens, usually in a selective way. Fungicides are used both in agriculture and to fight fungal infections in animals. Fungicide can be either contact or systemic. In agriculture, a contact fungicide kills fungi by direct contact; a systemic fungicide spreads internally through the plant, thereby killing the fungi.

As used herein, the term "bactericide" refers to a composition comprising one or more chemical substances or biological organisms capable of killing or inhibiting bacteria, usually in a selective way.

As used herein, the phrase "systemic acquired resistance (SAR)" refers to a "whole-plant" resistance response that occurs following an earlier localized exposure to a pathogen. SAR is analogous to the innate immune system found in animals, and there is evidence that SAR in plants and innate immunity in animals may be evolutionarily conserved. SAR is important for plants to resist disease, as well as to recover from disease once formed. SAR can be induced by a wide range of pathogens, especially (but not only) those that cause tissue necrosis, and the resistance observed following induction of SAR is effective against a wide range of pathogens. SAR is associated with the induction of a wide range of genes (so called PR or "pathogenesis-related" genes), and the activation of SAR often requires the accumulation of endogenous salicylic acid (SA). The pathogen-induced signal activates a molecular signal transduction pathway that is identified by a gene called NIM1, NPR1 or SAI1 (three names for the same gene) in the model genetic system *Arabidopsis thaliana*. SAR has been observed in a wide range of flowering plants, including dicotyledon and monocotyledon species.

As used herein, the phrase "defense proteins" refers to proteins that are differentially induced at the onset of systemic acquired resistance in a plant.

The present invention is directed to methods and compositions useful in inducing systemic acquired resistance (SAR) to infection in a plant. More specifically, the present invention uses a *Bacillus* control agent to induce SAR in plants. Plants in which SAR has been induced are capable of mounting defenses against a wide variety of infections. Thus, treatment of a plant with a *Bacillus* control agent that induces SAR would cause the plant to become more resistant to infections caused by such agents as fungi, bacteria or viruses. For example, treatment of a banana plant with a *Bacillus* control agent that induces SAR would result in a banana plant that is resistant to infection such as Black Sigatoka. In another embodiment, the systemic acquired resistance in the plant is induced through a salicylic acid independent and jasmonic acid dependent pathway. In one embodiment, the systemic acquire resistance is induced by *Bacillus mycoides* isolate BmJ through a NON-EXPRESSOR OF PATHOGENESIS-RELATED GENES1 (NPR1) dependent pathway. In another embodiment, the systemic acquired resistance is induced by *Bacillus mojavensis* isolate 203-7 through an NPR1 independent pathway.

Concerns related to the use of chemicals and genetically modified organisms (GMOs) as a means of managing crop diseases has prompted interest in methods of biological control. A non-pathogenic *Bacillus* control agent capable of inducing systemic resistance would provide a method of increasing disease resistance in a plant without the use of chemicals or GMOs. In addition, the absence of necrosis as a result of such application would be highly desirable. Additionally, it is also desirable to induce systemic resistance by foliar application of a microbe as foliar application provides ease of application and broader range of application methods and equipment.

The invention is also directed to methods of screening for biological control agents useful in inducing systemic acquired resistance to infection in a plant. Such methods as described herein would allow rapid detection of additional *Bacillus* control agents that can be used to induce systemic acquired resistance to infection in a plant.

Accordingly, the present invention provides methods of inducing systemic resistance to infection in plants with a *Bacillus* control agent. By "plant" is meant any organism belonging to the plant or vegetable kingdom. In further preferred embodiments, the plant is a banana, a cucurbit, (including, but not limited to, cucumbers, squash, pumpkins, and cantaloupes and other melons), a pecan, a sugar beet, or a geranium. "Plant" also encompasses parts of plants, as well as whole organisms. For example, the term plant encompasses a leaf or disc from a leaf, roots, stems, seeds, plant protoplasts, plant spores, plant shoots and plant cell cultures.

The plant being treated with *Bacillus* control agent is preferably capable of accumulating salicylic acid, although this may not be required in all cases. Salicylic acid accumulation is indicated for SAR signal transduction. Plants that do accumulate salicylic acid due to treatment with specific inhibitors, epigenetic repression of phenylalanine ammonia-lyase, or transgenic expression of salicylate hydroxylase, which specifically degrades salicylic acid, generally do not exhibit either SAR gene expression or disease resistance (Gaffney et al., 1993; Delaney et al., 1994; Mauch-Mani and Slusarenko 1996; Maher et al., Proc. Natl. Acad. Sci. USA 91, 7802-7806 (1994), incorporated herein by reference; Pallas et al., Plant J. 10, 281-293 (1996), incorporated herein by reference). Plants in which SAR can be induced by a *Bacillus* control agent include, for example, sugar beets, bananas, cucurbits, pecans, and geraniums.

Additionally, the plant being treated with *Bacillus* control agent is capable of producing defense proteins. By "defense proteins" is meant any protein that is differentially induced at the onset of systemic acquired resistance. Defense proteins include chitanases, β-1,3-glucanases, and peroxidases. Differential inducement of the defense proteins can be measured by an increase in the amount of defense proteins produced by the plant. Differential inducement can also be measured by an increase in the specific activity of the defense proteins. The increase in specific activity can be related to the presence of specific isoforms of the defense proteins. Additionally, differential inducement may also include differences in the normal ratios of the proteins relative to each other.

In addition to the production of defense proteins, systemic acquired resistance in the plant being treated is also preferably accompanied by a biphasic release of active oxygen species (AOS). Plants in which SAR has been induced exhibit an oxidative burst (Bargabus, et al., MPMI 16: 1145-1153 (2003), herein incorporated by reference). The oxidative burst is one of the earliest events in plant defense responses (Costet et al 2002). It is marked by the production of AOS through four sequential, one-electron reductions of dioxygen to water (Hippeli et al. 1999). The AOS include, in order of least to most reactive and longest to shortest lived, hydrogen peroxide, superoxide anion, and hydroperoxyl and hydroxyl radicals (Boveris 1998).

AOS are produced in both compatible and incompatible plant-pathogen interactions (Baker and Orlandi 1995; Glazener et al. 1996; Jabs et al. 1997; Wolfe et al. 2000). The production of hydrogen peroxide and superoxide anion also has been observed in rhizobium-plant interactions (Santos et al. 2001). In a compatible plant-pathogen interaction, a single, rapid burst of hydrogen peroxide is observed (Grant and Loake 2000). This response is believed to be due to the perception by the host of generic pathogen constituents, such as fungal glucans, chitins. or chitosans (Boller 1995), the conserved N-terminal region of bacterial flagella (Felix et al. 1999), or viral coat proteins (Allan et al. 2001). The transient primary burst is nonspecific and has no effect on disease progression (van Breusegem et al. 2001). During incompatible interactions, a second, more prolonged peak of hydrogen peroxide production quickly follows the initial burst as a result of specific gene-for-gene recognition (Baker and Orlandi 1995; Levine et al. 1994).

The present invention is directed to compositions and methods of inducing systemic resistance to infection, particularly pathogen infection, using a *Bacillus* control agent. By "systemic acquired resistance" (or "SAR") is meant a non-specific defense response of plants triggered following the induction of a hypersensitive response by an invading pathogen. SAR has been observed in both monocotyledenous and dicotyledenous plants and may be triggered by any type of invading pathogen (including bacteria, virus or fungus). The SAR response is non-specific in that it produces enhanced resistance to a broad spectrum of pathogens, regardless of the type of invading pathogen that triggered the response. It generally occurs throughout the plant, regardless of where the pathogen infection occurred. The SAR response usually begins within 2-10 days after the triggering pathogen invasion, and lasts for anywhere from several days to several weeks.

The present invention utilizes compositions comprising *Bacillus* control agents. By "*Bacillus* control agent" or "*Bacillus* biological control agent" herein is meant a *Bacillus* organism that can be used to eliminate or regulate the population of other living organisms, particularly relating to the regulation of pathogens in and on host plants. Preferred *Bacillus* control agents include those agents that induce systemic acquired resistance. In a preferred embodiment, the *Bacillus* control agent is a *Bacillus mycoides* isolate. In a further preferred embodiment, the *Bacillus* control agent is *Bacillus mycoides* isolate BmJ (accession number NRRL B-30890). In another preferred embodiment, the *Bacillus* control agent is a *Bacillus mojavensis* isolate. In a further preferred embodiment, the *Bacillus* control agent is *Bacillus mojavensis* isolate 203-7 (accession number NRRL B-30893). Additional preferred *Bacillus* control agents can be identified as outlined below.

The present invention provides methods of inducing systemic acquired resistance to pathogen infection in a plant. Thus, the methods of the invention are useful in preventing or treating infections which are caused by various microorganisms (e.g. pathogens) including, for example, bacteria, fungi, and viruses. The present invention provides methods of inducing disease resistance to infection in a plant, comprising applying a *Bacillus* control agent comprising *Bacillus mojavensis* isolate 203-7 and/or *Bacillus mycoides* isolate BmJ to the plant, wherein the plant is capable of producing defense proteins. In one embodiment, the disease resistance to infection is systemic acquired resistance. In another embodiment, the systemic acquired resistance in the plant is induced through a salicylic acid independent and jasmonic acid dependent pathway. In another embodiment, the systemic acquire resistance is induced by *Bacillus mycoides* isolate BmJ through a NON-EXPRESSOR OF PATHOGENESIS-RELATED GENES1 (NPR1) dependent pathway. In another embodiment, the systemic acquired resistance is induced by *Bacillus mojavensis* isolate 203-7 through a NPR1 independent pathway.

In one embodiment, the plant is a monocot. For example, the monocot plant is in the gramineae and cereal groups. Non-limiting exemplary monocot species include grains, tropical fruits and flowers, banana, maize, rice, barley, duckweed, gladiolus, sugar cane, pineapples, dates, onions, pineapple, rice, sorghum, turfgrass and wheat. In another embodiment, the plant is a dicot. For example, the dicot plant is selected from the group consisting of Anacardiaceae (e.g., cashews, pistachios), Asteraceae (e.g., asters and all the other composite flowers), Brassicaceae (e.g., cabbage, turnip, and other mustards), Cactaceae (e.g., cacti), Cucurbitaceae (e.g., watermelon, squashes), Euphorbiaceae (e.g., cassaya (manioc)), Fabaceae (e.g., beans and all the other legumes), Fagaceae (e.g., oaks), Geraniales (e.g., Geranium), Juglandaceae (e.g., pecans), Linaceae (e.g., flax), Malvaceae (e.g., cotton), Oleaceae (e.g., olives, ashes, lilacs), Rosaceae (e.g., roses, apples, peaches, strawberries, almonds), Rubiaceae (e.g., coffee), Rutaceae (e.g., oranges and other citrus fruits), Solanaceae (e.g., potato, tomato, tobacco), Theaceae (e.g., tea), and Vitaceae (e.g., grapes).

In another embodiment, the infection is caused by any kind of infectious (i.e., biotic) agents that affect plants. Examples of such agents/pathogens include but are not limited to an agent or pathogen selected from the group consisting of bacteria, fungi, and viruses. Examples of specific pathogens to be treated using the compositions and methods of the present invention include but are not limited to pathogens selected from the group consisting of *Mycosphaerella fijiensis* (Black sigatoka), *Cladosporium caryigenum* (pecan scab), *Glomerella cingulcaa* (Anthracnose), *Cercospora beticola* (Cercospora leaf spot), *Botrytis cinerea, Fusarium solani* f. sp. *cucurbitae* (Fusarium Crown rot), *Pseudomonas syringe* (angular leaf spot) and *Erwinia caratovora* (bacterial vascular necrosis).

Examples of bacteria that may cause infections treatable or preventable by inducing systemic resistance in a plant include *Pseudomonas* species, particularly *Pseudomonas aeruginosa, Pseudomonas fluorecens*, and *Pseudomonas* syringe (angular leaf spot). Other bacteria that may cause infections treatable or preventable by inducing systemic resistance in a plant include *Erwinia caratovora* (bacterial vascular necrosis), *Pantoua agglomorans, Erwinia tracheiphilia*, and *Zanthomonas axanopodis*. Depending on the species of bacteria and the tissue infected they produce and release enzymes that degrade cell walls, growth regulators that alter the plants' normal growth, toxins that degrade cell membranes and/or complex sugars that plug water conducting tissue. A general classification of phytopathogenic prokaryotes can be found below:

Kingdom: Procaryotae
- Bacteria—Have cell membrane and cell wall and no nuclear membrane
  - Division: Bacteria—Gram-positive
    - Class: Proteabacteria—Mostly single celled bacteria.
      - Family: Enterobacteriaceae
        - Genus: *Erwinia*, causing fire blight of pear and apple, Stewart's wilt in corn, and soft rot of fleshy vegetables.
        - *Pantoea*, causing wilt of corn.
        - *Serratia, S. marcescens*, a phloem-inhabiting bacterium causing yellow vine disease of cucurbits.
        - *Sphingomonas*, causing brown spot of yellow Spanish melon fruit.
      - Family: Pseudomonadaceae
        - Genus: *Acidovorax*, causing leaf spots in corn, orchids and watermelon.
        - *Pseudomonas*, causing numerous leaf spots, blights, vascular wilts, soft rots, cankers, and galls.
        - *Ralstonia*, causing wilts of solanaceous crops.
        - *Rhizobacter*, causing the bacterial gall of carrots.
        - *Rhizomonas*, causing the corky root rot of lettuce.
        - *Xanthomonas*, causing numerous leaf spots, fruit spots, blights of annual and perennial plants, vascular wilts and citrus canker.
        - *Xylophilus*, causing the bacterial necrosis and canker of grapevines.
      - Family: Rhizobiaceae
        - Genus: *Agrobacterium*, the cause of crown gall disease.
        - *Rhizobium*, the cause of nitrogen-fixing root nodules in legumes.
      - Family: still unnamed
        - Genus: *Xylella*, xylem-inhabiting, causing leaf scorch and dieback disease on trees and vines.
        - *Candidatus liherobacter*, Phloem inhabiting, causing citrus greening disease.
        - Unnamed, laticifer-inhabiting, causing bunchy top disease of papaya.
  - Division: Firmicutes—Gram-positive bacteria.
    - Class: Firmibacteria—Mostly single celled bacteria.
      - Genus: *Bacillus*, causing rot of tubers, seeds, and seedlings and white stripe of wheat.
      - *Clostridium*, causing rot of stored tubers and leaves and wetwood of elm and poplar.
    - Class: Thallobacteria—Branching bacteria.
      - Genus: *Arthrobacter*, causing bacterial blight of holly, thought to be the cause of Douglas-fir bacterial gall.
      - *Clavibacter*, causing bacterial wilts in alfalfa, potato, and tomato.
      - *Curtobacterium*, causing wilt in beans and other plants.
      - *Leifionia*, causing ratoon stunting of sugarcane.
      - *Rhodococcus*, causing fasciation of sweet pea.
      - *Streptomyces*, causing common potato scab.

More plant pathogenic bacteria are described in Robert W. Jackson, *Plant Pathogenic Bacteria: Genomics and Molecular Biology*, published by Horizon Scientific Press, 2009, ISBN 1904455379, 9781904455370; Samuel S. Gnanamanickam, *Plant-Associated Bacteria*, published by Springer, 2007, ISBN 1402045379, 9781402045370; Martin Dworkin et al., *The Prokaryotes: a handbook on the biology of bacteria*, Published by Springer, 2006, ISBN 0387254927, 9780387254920; George N. Agrios, *Plant pathology*, published by Academic Press, 2005, ISBN 0120445654, 9780120445653; and David W. Parry, *Plant pathology in*

*agriculture*, published by CUP Archive, 1990, ISBN 0521368901, 9780521368902.

Numerous classes of plant pathogenic fungi, including oomycetes, ascomycetes, and basidiomycetes, may cause infections treatable or preventable by inducing systemic resistance in a plant. Examples of fungi that may cause infections treatable or preventable by inducing systemic resistance in a plant include *Cercospora beticola* (Cercospora leaf spot), *Mycosphaerella fijiensis* (Black sigatoka), *Glomerella cingulata* (Anthracnose) and *Cladosporium caryigenum* (pecan scab). In general, fungal plant diseases can be classified into two types: those caused by soilborne fungi and those caused by airborne fungi. Soilborne fungi cause some of the most widespread and serious plant diseases, such as root and stern rot caused by *Fusarium* spp. And root rot caused by *Phytophthora* spp. For example, *Phytophthora parasitica* var. *nicotiana*, a soilborne oomycete found in many tobacco growing regions worldwide, causes black shank, a highly destructive root and stem rot disease of many varieties of cultivated tobacco. Since airborne fungi can be spread long distances by wind, they can cause devastating losses, particularly in crops which are grown over large regions. A number of pathogens have caused widespread epidemics in a variety of crops. Important diseases caused by airborne fungi are stem rust (*Puccinia graminis*) on wheat, corn smut (*Ustilago maydis*) on corn, and late blight disease (*Phytophthora infestans*) on potato and tomato. *Plasmopara viticola* is an airborne oomycete that causes downy mildew disease on grape vines. The blue mold fungus (*Peronospora tabacina*) has caused catastrophic losses in tobacco crops, particularly in the United States and Cuba. Most of these fungal diseases are difficult to combat, and farmers and growers must use a combination of practices, such as sanitary measures, resistant cultivars, and effective fungicide against such diseases. Billions of dollars are spent annually for chemical control of plant-pathogenic fungi. As a result, there is today a real need for new, more effective and safe means to control plant-pathogenic fungi, particularly oomycete, which are responsible for major crop loss.

Oomycetes is a class of Oomycota, which is a phylum of filamentous protists, containing over around 70 genera and more than 800 known species (J. W. Deacon *Modern mycology Edition:* 3, Published by Wiley-Blackwell, 1997 ISBN 0632030771, 9780632030774).

"Oomycota" means "egg fungi", referring to the oversize oogonia which house the female gametes (eggs). Despite the name and their superficial appearance, oomycetes are not fungi. They are unicellular heterokonts, physically resembling fungi. Oomycetes are commonly known as water molds (or water moulds) or downy mildew. They are microscopic, absorptive organisms that reproduce both sexually and asexually and are composed of mycelia, or a tube-like vegetative body (all of an organism's mycelia are called its thallus).

Oomycete cells differ from those of true fungi in that they have walls of cellulose and the amino acid hydroxyproline. They are heterotophic, either saphrophytic or parasitic. The principle cell wall of oomycetes is not composed of chitin, as in the fungi, but is made up of a mix of cellulosic compounds and glycan. The nuclei within the filaments are diploid, with two sets of genetic information, not haploid as in the fungi.

Oomycetes do not synthesize sterols. They have cillia (small hairlike structures) that help it eat and move around. Among the oomycetes, these are produced as asexual spores called zoospores, which are released from sporangium and capitalize on surface water (including precipitation on plant surfaces) for movement. Oomycetes may also germinate directly on the host plant by way of a germ tube. They also produce sexual spores, called oospores, that are translucent double-walled spherical structures used to survive adverse environmental conditions. This type of reproduction is known as "gametangical copulation". A few produce aerial asexual spores that are distributed by wind.

The water molds are economically and scientifically important because they are aggressive plant pathogens. Some species can cause disease in fish. The majority can be broken down into three groups, although more exist.

The *Phytophthora* group is a genus that causes diseases such as dieback, late blight in potatoes, sudden oak death, rhododendron root rot, and ink disease in the American Chestnut.

The *Pythium* group is even more prevalent than *Phytophthora* and individual species have larger host ranges, usually causing less damage. *Pythium* damping off is a very common problem in greenhouses where the organism kills newly emerged seedlings. Mycoparasitic members of this group (e.g. *P. oligandrum*) parasitize other oomycetes and fungi, and have been employed as biocontrol agents. One *Pythium* species, *Pythium insidiosum* is also known to infect mammals.

The third group of oomycetes is the downy mildews, which are easily identifiable by the appearance of white "mildew" on leaf surfaces.

Oomycete-caused plant diseases include, but are not limited to, grape downy mildew (caused by *Plasmopara viticola*) and potato late blight (caused by *Phytophthora infestans*) and oomycete infestation of Arctotis (caused by *Bremia lactucae*), Chenopodium murale (caused by *Peronospora farinosa*), cucurbits and cucumbers (caused by *Pseudoperonospora cubensis*), grasses and grains (caused by *Sclerospora graminicola*), lettuce (caused by *Bremia lactucae*), onion (caused by *Peronospora destructor*), alfalfa (caused by *Peronospora trifoliorum*), lima bean (caused by *Phytophthora phaseoli*), sunflower (caused by *Plasmopara halstedii*), carrot (caused by *Plasmopara nivea*, also called *Plasmopara crustosa*), hops (caused by *Pseudoperonospora humuli*), crucifers (caused by *Peronospora parasitica*), spinach (caused by *Peronospora effusa*), beet (caused by *Peronospora schachtii*, also called *Peronospora farinosa*), peas (caused by *Peronospora viciae*), rose (caused by *Peronospora sparsa*), poppy (caused by *Peronospora arborescens*), tobacco (caused by *Peronospora hyoscami*), and violet (caused by *Peronospora violae*).

Plant viruses are viruses affecting plants. Examples of viruses that may cause infections treatable or preventable by inducing systemic resistance in a plant include cucumber mosaic, tobacco mosaic, and barley yellow dwarf virus. Plant viruses are obligate intracellular parasites that do not have the molecular machinery to replicate without a host. Over 50% of known plant viruses are rod shaped (flexuous or rigid). The length of the particle is normally dependent on the genome but it is usually between 300-500 nm with a diameter of 15-20 nm. Protein subunits can be placed around the circumference of a circle to form a disc. In the presence of the viral genome, the discs are stacked, then a tube is created with room for the nucleic acid genome in the middle. The second most common structure amongst plant viruses are isometric particles. They are 40-50 nm in diameter. In cases when there is only a single coat protein, the basic structure consists of 60T subunits, where T is an integer. Some viruses may have 2 coat proteins are the associate to form an icosahedral shaped particle. There are three genera of Geminiviridae that possess geminate particles which are like two isometric particles stuck together. A very small number of plant viruses have, in addition to their coat proteins, a lipid envelope. This is derived from the plant cell membrane as the virus particle buds off from the cell. Non-limiting exemplary plant viruses species are Alfalfa mosaic virus (Alfamovirus), Apple chlorotic leaf spot virus (Trichovirus), Apple scar skin viroid (Viroids), Arabis mosaic virus (Nepovirus), Barley mild mosaic virus (Bymovirus), Barley stripe mosaic virus (Hordeivirus), Barley yellow mosaic virus (Bymovirus), Bean common mosaic virus (Potyvirus), Bean yellow mosaic virus (Potyvirus), Beet necrotic yellow vein virus (Furovirus), Blackeye cowpea mosaic virus (Potyvirus), Bean common mosaic virus (Potyvirus), Broad bean wilt virus (Fabavirus), Butterbur mosaic virus (Carlavirus), Carnation mottle virus (Carmovirus), Carnation vein mottle virus (Potyvirus), Cauliflower mosaic virus (Caulimovirus), Chrysanthemum mild mottle virus (Cucumovirus), Tomato aspermy virus (Cucumovirus), Chrysanthemum stunt viroid (Viroids), Citrus mosaic virus, Citrus tristeza virus (Closterovirus), Clover yellow vein virus (Potyvirus), Cocksfoot mottle virus (Sobemovirus), Cucumber green mottle mosaic virus (Tobamovirus), Cucumber mosaic virus (Cucumovirus), Cycas necrotic stunt virus (Nepovirus), Dasheen mosaic virus (Potyvirus), Grapevine Algerian latent virus (Tombusvirus), Konjac mosaic virus (Potyvirus), Melon necrotic spot virus (Carmovirus), Mulberry ringspot virus (Nepovirus), Narcissus mosaic virus (Potexvirus), Odontoglossum ringspot virus (Tobamovirus), Papaya ringspot virus (Potyvirus), Peach latent mosaic viroid, Peanut mottle virus (Potyvirus), Peanut stripe virus (Potyvirus), Bean common mosaic virus (Potyvirus), Peanut stunt virus (Cucumovirus), Potato virus A (Potyvirus), Potato virus M (Carlavirus), Potato virus S (Carlavirus), Potato virus X (Potexvirus), Potato virus Y (Potyvirus), Prune dwarf virus (Ilarvirus), Prunus necrotic ringspot virus (Ilarvirus), Radish mosaic virus (Comovirus), Rice black streaked dwarf virus (Fijivirus), Rice dwarf virus (Reovirus), Rice grassy stunt virus (Tenuivirus), Rice stripe virus (Tenuivirus), Rice tungro spherical virus (Sequivirus), Rice waika virus, Rice tungro spherical virus (Sequivirus), Ryegrass mottle virus, Satsuma dwarf virus (Nepovirus), Soil-borne wheat mosaic virus (Furovirus), Southern bean mosaic virus (Sobemovirus), Soybean mosaic virus (Potyvirus), Soybean stunt virus (Cucumovirus), Cucumber mosaic virus (Cucumovirus), Tobacco mosaic virus (Tobamovirus), Tobacco mosaic virus (Tobamovirus), Tomato mosaic virus (Tobamovirus), Tobacco necrosis virus (Necrovirus), Tobacco rattle virus (Tobravirus), Tobacco ringspot virus (Nepovirus), Tomato aspermy virus (Cucumovirus), Tomato black ring virus (Nepovirus), Tomato mosaic virus (Tobamovirus), Tomato ringspot virus (Nepovirus), Tomato spotted wilt virus (Tospovirus), Turnip mosaic virus (Potyvirus), Watermelon mosaic virus 1 (Potyvirus), Papaya ringspot virus (Potyvirus), Watermelon mosaic virus 2 (Potyvirus), Wheat yellow mosaic virus (Bymovirus), Zucchini yellow mosaic virus (Potyvirus). More plant viruses have been described in F. C. Bawden, *Plant Viruses and Virus Diseases*, Publisher Biotech Books, 2002, ISBN 8176220647, 9788176220644, which is incorporated herein by its entirety for all purposes.

In one embodiment of the invention, systemic acquired resistance to infection is induced by applying to the foliage of the plant a composition comprising a *Bacillus* control agent.

The *Bacillus* control agent is applied to the foliage of the plant by methods known in the art. For example, the *Bacillus* control agent may be applied aerially. In this method, the *Bacillus* control agent is sprayed from above the plants, for example from an airplane. The concentration of the *Bacillus* control agent applied aerially is $10^3$-$10^{12}$ cfu ("colony forming units")/ml, more preferably $10^4$-$10^{10}$ cfu/ml, even more preferably $10^5$-$10^9$ cfu/ml, most preferably $10^8$ cfu/ml. The *Bacillus* control agent can be applied at a wide range of volume/acre of plants treated. For example, the *Bacillus* control agent may be applied at 1-100 gallons/acre, preferably 2-50 gallons/acre, more preferably 5-10 gallons/acre, still more preferably 6-8 gallons/acre, most preferably 7 gallons/acre.

The *Bacillus* control agent can also be applied from the ground, for example by any agricultural spray equipment, such as, for example, an orchard spray mechanism. An orchard spray mechanism is any sprayer, either manual or automatic, that can be used to apply the *Bacillus* control agent to the foliage of a plant. The concentration of the *Bacillus* control agent applied from the ground is $10^3$-$10^{12}$ cfu/ml, more preferably $10^4$-$10^{10}$ cfu/ml, even more preferably $10^5$-$10^9$ cfu/ml, most preferably $10^7$ cfu/ml. The *Bacillus* control agent can be applied from the ground at a wide range of volume/acre of plants treated. For example, the *Bacillus* control agent may be applied at 10-500 gallons/acre, preferably 10-100 gallons/acre, most preferably 20 gallons/acre.

In one embodiment, the *Bacillus* control agent is applied to the plants as a spray-dried formulation suspended in an aqueous solution. In another embodiment, the *Bacillus* control agent is applied as freshly grown cells. In another preferred embodiment the *Bacillus* control agent is formulated with a carrier to aid dilution and dispersion, wherein such a carrier could include various types of clay such as attaclay.

In a preferred embodiment, after the *Bacillus* control agent has been applied to the plant, particularly to the foliage of the plant, it proceeds to colonize the plant; particularly the plant phyllosphere.

In a further preferred embodiment of the invention, the *Bacillus* control agents of the invention do not induce necrotic cell death as a result of inducing systemic acquired resistance. By "cell necrosis" or "necrotic cell death" or grammatical equivalents herein is meant cell death that occurs at the site of application (e.g. the foliage) of an agent that causes such necrosis. Plants are examined for necrosis by observation of leaves by microscope, and by staining techniques that selectively stain for dead cells. One of the problems associated with known agents that induce systemic resistance is necrotic cell death that occurs at the site of application of the agents. Unlike these agents, the application of the *Bacillus* control agent does not cause necrotic cell death.

The present invention also provides methods of inducing disease resistance to infection in a plant further comprising applying a second biological or chemical control agent. In one embodiment, the second biological or chemical control agent is antibacterial. In another embodiment, the second biological or chemical control agent is antifungal. In another embodiment, the second biological or chemical control agent is antiviral. In another embodiment, the second biological or chemical control agent is a plant activating agent. In another embodiment, the second biological or chemical control agent is a pesticide. Commonly used bactericides, fungicides, virucides, plant activating agents and pesticides are described below.

Non limiting exemplary bactericides include, active chlorine (i.e., hypochlorites, chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated non-ionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride etc.

Commonly used fungicides include, but are not limited to, benomyl, TPTH, propiconazole, tetraconazole, benimidazoles, triazoles, strobilurins, carboxamides, sulfananilides, phenylsulfamides, azoles, nitrogenous heterocycles, dicarboximides, phthalimides, carbamates, thiocarbamates, formaidines, antibiotics, aromatics, guanidines, organochlorine compounds, organometallics, organophosphorus compounds, nitrophenyl compounds, sulfur heterocyclyl compounds, ureas, inorganics, and others (e.g., benzamacril, carvone, essential oil extract from plants, cedar leaf oil, neem oil, chloropicrin, DBCP, drazoxolon, fenaminosulf, metzoxolon, oxolinic acid, spiroxamine, cymoxanil, metrafenone. Prohexadione calcium, thicyofen, dithane, chlorothalanil, dichlorophen, dicloran, nitrothal-isopropyl, bronopol, diphenylamine, mildiomycin, oxin-copper, cyflufenamide (e.g., N-(cyclopropylmethoxyimino-(6-difluoromethoxy-2,3-difluorophenyl)-methyl)-2-phenylaceta-mide), UK-2A (antibiotic isolated from *Streptomyces* sp. 517-02).

Plant activating agents are natural or synthetic substances that can stimulate, maintain, or enhance plant resistance to biotic and/or abiotic stressors/pressures, which include, but are not limited to, acibenzolar, probenazole, isotianil, salicyclic acid, azelaic acid, hymexazol, brassinolide, forchlorfenuron, benzothiadiazole (e.g., ACTIGARD® 50WG), microbes or elicitors derived from microbes, More plant activating agents are described in U.S. Pat. Nos. 6,849,576, 5,950,361, 6,884,759, 5,554,576, 6,100,092, 6,207,882, 6,355,860, 5,241,296, 6,369,296, 5,527,783, and 6,987,130. Microbes, or chemical compounds and peptides/proteins (e.g., elicitors) derived from microbes, can also be used as plant activating agents. Non-limiting exemplary elicitors are: branched-β-glucans, chitin oligomers, pectolytic enzymes, elicitor activity independent from enzyme activity (e.g. endoxylanase, elicitins, PaNie), avr gene products (e.g. AVR4, AVR9), viral proteins (e.g. vial coat protein, Harpins), flagellin, protein or peptide toxin (e.g. victorin), glycoproteins, glycopeptide fragments of invertase, syringolids, Nod factors (lipochitooligo-saccharides), FACs (fatty acid amino acid conjugates), ergosterol, bacterial toxins (e.g. coronatine), and sphinganine analogue mycotoxins (e.g. fumonisin B1). More elicitors are described in Howe et al., *Plant Immunity to Insect Herbivores*, Annual Review of Plant Biology, 2008, vol. 59, pp. 41-66; Stergiopoulos, *Fungal Effector Proteins Annual Review of Phytopathology*, 2009, vol. 47, pp. 233-263; and Bent et al., *Elicitors, Effectors, and R Genes: The New Paragigm and a Lifetime Supply of Questions*, Annual Review of Plant Biology, 2007, vol. 45, pp. 399-436.

Thus, it is another aspect of this invention to apply a biological or chemical control agent in addition to the *Bacillus* control agent applied to induce systemic acquired resistance to infection in a plant. There are a number of control agents that can be combined with the agents of the invention, including biological and chemical control agents.

Biological control agents are living organisms which can be used to eliminate or regulate the population of other living organisms. Biological control agents can be, for example, antibacterial agents, antifungal agents, antiviral agents, and insecticides. Examples of biological control agents include, but are not limited to, *Bacillus mycoides, Bacillus pumulis, Bacillus thuringiensis* (Bt), *Bacillus Iiquefacians*, numerous species of *Pseudomonas* bacteria, *Seratia marcesans*, and *Pantoua agglomerans*. Biological control agents include those agents that induce systemic acquired resistance, although this is not required in the combination treatments outlined herein.

Chemical control agents are chemical substances which can be used to eliminate or regulate the population of living organisms. Chemical control agents can be, for example, antibacterial agents, antifungal agents, antiviral agents, and insecticides. Examples of chemical control agents include, but are not limited to, triphenyltin hydroxide (TPTH, Super-Tin, Griffin LLC), propiconazole (Tilt, Syngenta Crop Protection, Inc) and tetraconazole (Eminent, Sipeam Agro USA Inc.), benomyl, Strobilurin fungicides including Azoxystrobilurin (Syngenta), Trifioxstrobilurin (Bayer), Pyracstrobilurin (BASF) and Chlorthalonil fungicides. Chemical control agents may be applied as outlined herein to the foliage in combination with or alternating with the *Bacillus* control agent. Combinations with the *Bacillus* control agent and the chemical fungicide used at ¼ of the recommended label rate have provided disease control equivalent to the chemical fungicide used at the full rate. Chemical control agents include those agents that induce systemic acquired resistance, although this is not required in the combination treatments outlined herein.

In one embodiment of the invention, the *Bacillus* control agent is applied in conjunction with the application of the biological or chemical control agent. In this embodiment, the *Bacillus* control agent is mixed with the biological or chemical agent and applied simultaneously to the plant. Alternatively, the *Bacillus* control agent and biological or chemical control agent are applied separately but simultaneously to the plant. Additionally, the *Bacillus* control agent may be applied after the biological or chemical control agent has been applied to the plant but during the time the biological or chemical control agent is still acting as a control agent. The biological or chemical control agent may also be applied after the application of the *Bacillus* control agent plant but during the time the *Bacillus* control agent is still acting to induce systemic acquired resistance in the plant.

In further embodiments, the *Bacillus* control agent is applied sequentially with the biological or chemical control agent. In one of these embodiments, the *Bacillus* control agent is applied to the plant and induces systemic acquired resistance before the application of the biological or chemical control agent. The systemic acquired resistance induced by the *Bacillus* control agent mayor may not be present when the biological or chemical control agent is applied. Alternatively, the biological or chemical control agent is applied to the plant before the *Bacillus* control agent. The biological or chemical control agent mayor may not still be acting as a control agent when the *Bacillus* control agent is applied. This sequential application may be repeated.

According to one embodiment, when the biological or chemical control agent is an antibacterial agent it is preferable that the antibacterial agent is applied prior to the application of the *Bacillus* control agent such that the *Bacillus* control agent is not effected by the antibacterial agent.

In one embodiment, the *Bacillus* control agent is harvested from the plant it has colonized and is then used to induce systemic resistance in plants, a process referred to as host passage. *Bacillus* control agents that have undergone host passage have been shown to be more effective in inducing systemic resistance than those same agents prior to host passage. This may be done reiteratively as well.

It is another aspect of the invention to provide a plant to which a *Bacillus* control agent has been applied. A plant to which a *Bacillus* control agent has been applied is also referred to as a plant "treated" with a *Bacillus* control agent. In a preferred embodiment, the *Bacillus* control agent is applied to the foliage of the plant. In a further preferred embodiment, the phyllosphere of the plant is colonized by the *Bacillus* control agent. In a further preferred embodiment the plant treated with a *Bacillus* control agent is a banana, a cucurbit, a pecan, a sugar beet, or a geranium.

In one embodiment of this aspect of the invention provides for a banana plant treated with a *Bacillus* control agent. In another embodiment, the banana plant is treated with *Bacillus mycoides*. In a further embodiment, the banana plant is treated with *Bacillus mycoides* isolate BmJ (accession number NRRL B-30890). In another embodiment, the banana plant is treated with *Bacillus mojavensis*. In yet a further embodiment, the banana plant is treated with *Bacillus mojavensis* isolate 203-7 (accession number NRRL B-30893). In each of these embodiments, the phyllosphere of the banana plant can be colonized by the *Bacillus* control agent.

In another embodiment of this aspect of the invention provides for a cucurbit plant treated with a *Bacillus* control agent. In one embodiment, the cucurbit plant is treated with *Bacillus mycoides*. In a further embodiment, the cucurbit plant is treated with *Bacillus mycoides* isolate BmJ (accession number NRRL B-30890). In another embodiment, the cucurbit plant is treated with *Bacillus mojavensis*. In yet a further embodiment, the cucurbit plant is treated with *Bacillus mojavensis* isolate 203-7 (accession number NRRL B-30893). In each of these embodiments, the phyllosphere of the cucurbit plant can be colonized by the *Bacillus* control agent.

Another embodiment of this aspect of the invention provides for a pecan plant treated with a *Bacillus* control agent. In one embodiment, the pecan plant is treated with *Bacillus mycoides*. In a further embodiment, the pecan plant is treated with *Bacillus mycoides* isolate BmJ (accession number NRRL B-30890). In another embodiment, the pecan plant is treated with *Bacillus mojavensis*. In yet a further embodiment, the pecan plant is treated with *Bacillus mojavensis* isolate 203-7 (accession number NRRL B-30893). In each of these embodiments, the phyllosphere of the pecan plant can be colonized by the *Bacillus* control agent.

Another embodiment of this aspect of the invention provides for a geranium plant treated with a *Bacillus* control agent. In one embodiment, the geranium plant is treated with *Bacillus mycoides*. In a further embodiment, the geranium plant is treated with *Bacillus mycoides* isolate BmJ (accession number NRRL B-30890). In another embodiment, the geranium plant is treated with *Bacillus mojavensis*. In yet a further embodiment, the geranium plant is treated with *Bacillus mojavensis* isolate 203-7 (accession number NRRL B-30893). In each of these embodiments, the phyllosphere of the geranium plant can be colonized by the *Bacillus* control agent.

Another embodiment of this aspect of the invention provides for a strawberry or a grape plant treated with a *Bacillus* control agent. In one embodiment, the strawberry or the grape plant is treated with *Bacillus mycoides*. In a further embodiment, the strawberry or the grape plant is treated with *Bacillus mycoides* isolate BmJ (accession number NRRL B-30890). In another embodiment, the strawberry or the grape plant is treated with *Bacillus mojavensis*. In yet a further embodiment, the strawberry or the grape plant is treated with *Bacillus mojavensis* isolate 203-7 (accession number NRRL B-30893). In each of these embodiments, the phyllosphere of the strawberry or the grape plant can be colonized by the *Bacillus* control agent.

Another embodiment of this aspect of the invention provides for a wheat plant treated with a *Bacillus* control agent. In one embodiment, the wheat plant is treated with *Bacillus mycoides*. In a further embodiment, the wheat plant is treated with *Bacillus mycoides* isolate BmJ (accession number NRRL B-30890). In another embodiment, the wheat plant is treated with *Bacillus mojavensis*. In yet a further embodiment, the strawberry or the grape plant is treated with *Bacillus mojavensis* isolate 203-7 (accession number NRRL B-30893). In each of these embodiments, the phyllosphere of the wheat plant can be colonized by the *Bacillus* control agent.

Embodiments of the invention include plants treated with the *Bacillus* control agent as well as parts of the plants so treated. For example, a banana leaf or disc from a banana leaf treated with a *Bacillus* control agent is contemplated in this embodiment. Similarly, a plant protoplast, plant spore or plant shoot or plant cell culture treated with a *Bacillus* control agent is contemplated in this embodiment.

Another aspect of the invention provides for methods of screening for biological control agents that induce systemic resistance to a disease in a plant. Currently used means of demonstrating induction of SAR in plants include challenge assays in which distal untreated leaves are challenged with a pathogen following a short priming period with an inducing agent on a primarily, spatially separated leaf or root system (Conrath, et al 2000, herein, incorporated by reference). Challenge assays, however, are time-consuming and difficult to adapt to screening of multiple agents.

One embodiment of the invention provides for a method of screening for a biological control agent that induces systemic resistance in a plant comprising contacting a plant sample with a biological control agent and detecting the release of active oxygen species (AOS) in the sample. Biphasic production of AOS precedes induction of systemic resistance (Wolfe, et al. 2000) and therefore hydrogen peroxide production patterns serve as an indicator of SAR induction capability. In a preferred embodiment, the release of AOS is detected by a phenol red oxidation assay.

Another embodiment of the invention provides for a method of screening for a biological control agent that induces systemic resistance in a plant comprising contacting a plant sample with a biological control agent and detecting for the presence of defense proteins, including, but not limited to, chitinase, β-1,3-glucanse, and peroxidase.

One embodiment provides for a method of screening for a biological control agent that induces systemic resistance in a plant comprising contacting a plant sample with a biological control agent and detecting for the presence of chitinase in the sample. While certain chitinases are present in plants that have not been induced for systemic acquired resistance, overall levels of chitinase activity are increased in plants that have been treated to induce SAR. Additionally, certain isoforms of chitinase have increased specific activity in plants treated to induce SAR.

The presence of chitinase can be determined by monitoring the degradation of chitin by various methods. In one embodiment, the chitinase activity is determined by a glycol chitin plate assay. Glycol chitin plate assays can be performed by first extracting protein from the plant treated with the *Bacillus* control agent and then incubating the extract on an agarose plate containing glycol chitin infused with a fluorescent brightener. The presence of non-fluorescent lytic zones is indicative of chitinase activity. Specific activity of the chitinase can be determined by including a series of standards (Bargabus, R. L., et al., Physiol. Mol. Plant. Pathol. 61:289-298, 2002), herein incorporated by reference). The presence of chitinase can also be determined by monitoring a decrease in fluorescence against time of a solution containing chitin and a fluorescence brightener, such as Calcofluor White M2R, to which a protein extract to be tested for chitinase activity has been added (Sampson M. N., et al, Microbiology, 144:2189-2194 (1998), herein incorporated by reference). Additional methods of measuring chitinase activity include monitoring of degradation of fluorogenic chitinase substrates or radio-labeled chitin substrates (Sampson M. N., et al, Microbiology, 144:2189-2194 (1998)). The presence of chitinase may also be detected using immunoassays. Any of the assays that monitor a detectable signal, such as fluorescence, may be performed in microtiter plates and are amenable to use in high throughput screening.

A further embodiment provides for a method of screening for a biological control agent that induces systemic resistance in a plant comprising contacting a plant sample with a biological control agent and detecting for the presence of β-1,3-glucanase in the sample. While certain β-1,3-glucanase are present in plants that have not been induced for systemic acquired resistance, overall levels of β-1,3-glucanase activity are increased in plants that have been treated to induce SAR. Additionally, certain isoforms of β-1,3-glucanase have increased specific activity plants treated to induce SAR.

The presence of β-1,3-glucanase can be determined by monitoring the degradation of beta-glucan polysaccharide by various methods. In a preferred embodiment, the β-1,3-glucanase activity is determined by an aniline blue plate assay. Aniline blue plate assays can be performed by first extracting protein from the plant treated with the *Bacillus* control agent and then incubating the extract on an agarose plate containing analine blue and laminarin. The presence of pink lytic zones on a blue background is indicative of β-1,3-glucanase activity. Specific activity of the β-1,3-glucanase can be determined by including a series of standards (Bargabus, R. L., et al., Biological Control, In Press, herein incorporated by reference). Additional methods of measuring β-1,3-glucanase activity include monitoring of degradation of fluorogenic β-1,3-glucanase substrates (such as dansyl-labeled laminarin) or radio-labeled β-1,3-glucanase substrates. The presence of β-1,3-glucanase may also be detected using immunoassays. Any of the assays that monitor a detectable signal, such as fluorescence, may be performed in microtiter plates and are amenable to use in high throughput screening.

A further embodiment of the invention provides for a method of screening for a biological control agent that induces systemic resistance in a plant comprising contacting a plant sample with a biological control agent and detecting both the chitinase activity and the β-1,3-glucanase activity in the sample. In a preferred embodiment, the chitinase activity is determined by a glycol chitin plate assay and the β-1,3-glucanase activity is determined by an aniline blue plate assay. Other methods may be used to detect the activity of chitinase and β-1,3-glucanase as discussed above.

The methods of screening for biological control agents that induce systemic resistance as described above may also be used to screen chemical control agents that induce systemic resistance.

The invention having been described, it will be apparent to ordinarily skilled artisans that numerous changes and modifications can be made thereto without departing from the spirit or the scope of the appended claims.

All publications and patents cited herein are expressly incorporated by reference for all purposes.

Deposit Information

On Jan. 4, 2006, Applicants made a deposit of *Bacillus mycoides* isolate 'BmJ' (aka 'Isolate J') under the Budapest Treaty with the Agricultural Research Service Culture Collection (NRRL), 1815 North University Street, Peoria, Ill. 61604, USA, as Accession Number NRRL B-30890.

EXAMPLES

Example 1

Isolation and Testing of *Bacillus mycoides* Isolate BmJ

*Bacillus mycoides* isolate J (BmJ) was isolated from sugar beet leaves as follows. Leaf samples from sugar beets plants that had reduced infection by *Cercospora beticola* (CB), the fungal pathogen that is the causal agent of *Cercospora* leaf spot, were collected from a sugar beet field. in Sydney Mont. The leaves were washed and pasteurized. Endospores were isolated from the pasteurized wash. The endospores were grown and tested for the ability to induce resistance to CB in sugar beets. One of the isolates, BmJ, was selected for use as a biological control agent because it provided the best control of isolates tested in early glasshouse trials.

In preliminary studies, a spontaneous Rifampicin resistant mutant of BmJ, that did not differ in growth rate or disease control capabilities from BmJ, was utilized in repeated attempts to isolate BmJ at 3, 6, 9, and 18 d post treatment from distal untreated and treated sugar beet leaves and petioles (Jacobsen, unpublished work). Due to the low level of BmJ populations on treated leaf surfaces and the lack of Rifampicin mutants isolated from distal untreated leaves, it was concluded that the level of disease control from BmJ treatment could not be due to direct effects of BmJ on CB (Bargabus, et al., Physiological an Molecular Plant Pathology, 61:289-298 (2002), herein incorporated by reference).

Example 2

Testing of BmJ in Growth Chamber Experiments

BmJ Preparation

*B. mycoides* isolate J (BmJ) cells, originally isolated from sugar beet leaves from Sidney, Mont. in 1994, were stored at −80° C. in 10% glycerol and I tryptic soy broth (TSB) (Difco). For fresh cell preparations, BmJ was cultured in TSB for 48 h (28° C.). Cells were centrifuged 15 min at 10000 g (4° C.), washed with sterile water (2×), then resuspended in distilled water. The optical density was adjusted to A600 1.0, then diluted 1:2 based on optical density curves confirmed by dilution plating. This optical density and dilution provided for approximately $1 \times 10^8$ cfu/ml. The precise number of cells was not determined due to the chain-forming nature of the organism. For experiments testing dead cells, BmJ was autoclaved in water for 30 min following washing. Autoclaved cells were tested for lack of viability by plating 100 microliters onto three plates of 50% tryptic soy agar (TSA). For field studies, either fresh BmJ cells prepared as described above or a spray-dried formulation, containing $2 \times 10^{13}$ cfu/g before dilution, prepared by Chris Hanson Labs (Milwaukee, Wis., U.S.A.) were used.

Fungal Culture

*C. beticola* (GB) (wild type isolate EC3, isolated in Sidney, Mont. in 1996) was grown on V-8 agar for a minimum of two weeks with exposure to fluorescent or natural light for at least one week to promote sporulation. Spores were harvested at approximately 30 days after plating in 0.1 carboxymethyl cellulose by scraping with a cotton swab, counted with a haemocytometer and adjusted to $1 \times 10^4$ spores/ml.

Plant Culture

Sugar beet varieties Holly Hybrid (HH) 88 (hybrid) and Seedex 920002 (inbred) were seeded into flats for germination, transplanted into 4" pots after I week, and grown in the glasshouse for 6 weeks in MSU mix (⅓ sand, ⅓ peat and ⅓ topsoil plus the wetting agent Aquagrow 2000, Aquatrols, Cherry Hill, N.J.). Plants were maintained at 24±2° C. and were watered daily and fertilized twice a week to maintain vigorous growth. Photoperiod was 16 h light and 8 h dark.

Growth Chamber Experiments

For growth chamber experiments, the leaf penultimate to the oldest two true leaves of sugar beet plants, in replicates of 10, was treated with BmJ, Acibenzolar-5-methyl (ASM, 50 ppm a.i.; ActigardS50 WG, Syngenta, Greensboro, N.C.), or dead BmJ in 3-glucan with an aerosol sprayer. After drying, the treated leaf was covered with a plastic bag to ensure spatial separation from CB. The susceptible sugar beets were incubated for three days which was previously determined to be the timing that provided the best level of disease control [5], at which time the remainder of the leaves were challenged with the fungal pathogen CB ($10^4$ spores $ml^{-1}$), which was applied to near run-off using an aerosol sprayer. After treatment, plants were transferred to a 28° C. growth chamber equipped with plastic tents and humidifiers. Plants were kept at 100 humidity for 72 h following inoculation with CB. Disease severity was calculated according to the KWS scale [20] and disease reduction was determined for the various inducing agents at 14 and 21 days post inoculation.

To determine the effectiveness of BmJ at reducing disease severity of *Cercospora* leaf spot on sugar beet while spatially separated from CB, the distal untreated leaves of BmJ-treated plants were challenged with CB 3 d post treatment. ASM and dead BmJ in 10 (3-glucan were also used as treatments before fungal challenge as positive and negative controls, respectively. All plants were rated using the KWS (1-9) scale at 14 and 21d post challenge.

Results

The more susceptible of the two cultivars of sugar beet tested (HH88, a hybrid), resulted in the greatest systemic reduction in disease severity (–80% reduction) following priming with BmJ (Table 1). The decreased occurrence of leaf spot symptoms was statistically significant in comparison to the negative control (dead BmJ treatment), but not statistically different from the 63.6% reduction resulting from ASM treatment (Table 1). Priming HH88 sugar beets with virulent CB did not statistically reduce disease symptoms (Table 1). The inbred sugar beet cultivar (Seedex 920002) was less susceptible than its hybrid counterpart, and the overall disease severity was lower. With the inbred cultivar, BmJ was less effective than ASM-pretreatment, however the approximate 2% difference was not statistically significant (Table 1). The 66.7% reduction in disease severity noted with the inbred variety following BmJ treatment was statistically higher when compared to the negative (dead BmJ) control pretreatment (Table 1). Dead BmJ cells in p-glucan were not effective at controlling disease when applied to either cultivar when compared to untreated controls (data not shown) and plants not challenged with CB showed no infection (Bargabus, et al., Physiological an Molecular Plant Pathology, 61:289-298 (2002)).

TABLE 1

Systemic disease control of Cercospoa leaf spot on two different cultivars of sugar beet using *B. mycoides* isolate BmJ and acibenzolar-S-methyl in glasshouse experiments

| | Disease Severity | | | | | |
|---|---|---|---|---|---|---|
| | HH88[a] | | Seedex[a] | | % Reduction at 21 DPC[b] | |
| Treatment[c] | 14 DPC | 21 DPC | 14 DPC | 21 DPC | HH88[a] | Seedex[a] |
| Control[d] | 5.76 | 14.34 | 0.32 | 0.48 | n.r. | n.r. |
| *C. beticola* | 5.24 | 14.10 | n.d. | n.d. | n.r. | n.r. |
| Acibenzolar-S-methyl | 0.76 | 5.26 | 0.16 | 0.17 | 63.6 | 64.6 |
| *B. mycoides* | 1.03 | 2.94 | 0.13 | 0.16 | 79.5 | 66.7 |
| LSD (0.05)[e] | 2.87 | 3.78 | 0.09 | 0.12 | n.d. | n.d. |

[a]Holly Hybrid 88 (HH88, hybrid) and Seedex 920002 (Seedex, inbred) were the two sugar beet cultivars used in glasshouse experiments.

[b]DPC = days post challenge with *C. betieo/a*.

[c]Plants were treated with dead *B. mycoides* isolate BmJ in (3-glucan (control), *C. betieola* (virulent on HH88 and Seedex), acibenzolar-S-methyl, or live *B. myeoides* isolate BmJ on one leaf, then challenged 3 days later with *e. betieo/a*, the fungal pathogen, on the distal untreated leaves.

[d]Control = dead *B. myeoides* isolate BmJ cells applied with (3-glucan.

[e]LSD = least significant difference (probability = 0.05).

Example 3

Testing of BmJ in Field Studies

Field Studies

Field studies were conducted at the Eastern Agricultural Research Center in Sidney, Mont. from 1996 through 2003. Sugar beet variety 'Beta 1996' was planted the first year, VIM 66140 was planted the second year, 1-11-188 the third year, KW2262 the fourth year and Beta 2185 the fifth, sixth, and seventh years. All cultivars were equally susceptible to *C. beticola* infection (BetaSeed, Shakopee, Minn., U.S.A.). A spray-dried formulation of BmJ, suspended in water ($10^8$ cfu/ml), was used the first four years. In the last two years, freshly grown, washed cells were harvested from a 24 h tryptic soy broth culture grown at room temperature and prepared as described above, and applied to the plants. Fungicide treatments included triphenyltin hydroxide (TPTH, SuperTin, Griffin L.L.C.), propiconazole (Tilt, Syngenta Crop Protection, Inc) and tetraconazole (Eminent, Sipeam Agro USA Inc.) that were applied at 390, 253 and 876 g ai $ha^{-1}$, respectively. All treatments were applied at 1761 $ha^{-1}$ using a $CO_2$ backpack sprayer with a 4-nozzle boom starting at disease onset and continued at 14 day intervals for a total of four sprays. Plots were arranged "in a randomized complete block design with six replicates per treatment. Each block consisted of 6 rows (9.2 m long) spaced 56 cm apart, resulting in a plant density of approximately 100 000 plants $ha^{-1}$. The four middle rows from each block were treated, leaving the outside two rows of each block as border rows. One middle row from each block for each treatment was harvested for yield data. Disease evaluations were taken four times during the growing season and 100 leaves/replicate were rated using the KWS scale from 1 to 9 [20]. Area under the disease progress curve (AUDPC) was calculated for treated and untreated plants and percent disease control was determined as follows: 1–(diseases severity of untreated controls/disease severity of treated plants)*100.

To examine the efficacy of BmJ under field conditions, the biological control agent treatment was extended to the field. Several fungicide treatments were introduced 10 to make comparisons between BmJ and current control methods. The KWS scale was used to rate CB disease severity for consistency with glasshouse data.

Results

Field application of BmJ resulted in disease control superior to untreated control plants (38-91% reduction) and equivalent to the chemical disease control triphenyltin hydroxide (TPTH; 253 g/ha) in 2 (1997 and 2000) of the 6 years (Table 2). BmJ also produced similar disease control to propiconazole (Tilt; 104 g/ha) in 2 (1996 and 1997) of 3 years (Table 2). BmJ, applied in conjunction with Tilt, significantly improved CB disease control over Tilt alone in 1997. Overall, under all conditions tested, BmJ alone or in combination with Tilt was just as effective against CB as TPTH, the most widely used fungicide (Table 2). Measurement of the area under the disease progress curve (AUDPC) over 5 years for untreated controls showed that all treatments worked just as well under severe disease conditions as they did in years with less disease pressure (Table 2) (Bargabus, et al., Physiological an Molecular Plant Pathology, 61:289-298 (2002)).

TABLE 2

Multi year analysis of Cercospora leaf spot reduction in the field using B. mycoides isolate BmJ, triphenyltin hydroxide and propiconazole or tetraconazole
Disease Reduction by Year[a]

| Treatment | 1996[b] | 1997 | 1998 | 1999 | 2000 | 2001 |
|---|---|---|---|---|---|---|
| B. mycoides | 62 | 81 | 51 | 66 | 91 | 38 |
| TPTH (390 g a.i.ha$^{-1}$) | 81 | 90 | 81 | 94 | 72 | 88[b] |
| B. mycoides + Tilt (253 g a.i.ha$^{-1}$) | 78 | 89 | 76 | 97 | 91 | 80[c] |
| Tilt (253 g a.i.ha$^{-1}$) | 68 | 72 | 82 | n.d. | n.d. | n.d. |
| LSD (0-05)[e] | 14 | 13 | 21 | 14 | 34 | 15 |
| AUDPC[f] | 330 | 220 | 176 | 30 | 17 | 73 |

[a]Percent disease control in untreated plots was zero.
[b]Sugar beet variety 'Beta 1996' was planted in 1996, variety VDH 66140 was planted in 1997, variety HH88 was planted in 1998, variety KW2262 was planted in 1999, and variety 'Beta 2185' was planted in 2000 and 2001, all of which are equally susceptible to C. betieo/a (BetaSeed).
[c]Fungicide treatment in 2001 was Eminent instead of TPTH.
[d]in the year 2001, B. myeoides was applied with tetraconazole (Eminent) (876 g a.i. hao,) instead of propaconazole (Tilt).
[e]ISD = least significant difference (probability = 0.05).
[f]AUDPC = area under the disease progress curve for C. betieo/a. AUDPC represents the disease severity during the field treatment years in untreated controls (higher number = more disease).
n.d. = no data.

Example 4

Disease Reduction Capabilities of B. Mycoides and B. Pumulis Isolates

Bacterial Cultures

Bacillus myeoides isolate J (BmJ) was originally isolated from the phylioplane of sugar beet. B. pumilus isolates 203-11.341-21-15.203-6, 341-20-14, 241-20-1, 203-3, 203-4, and 341-16-5 and B. mojavensis isolate 203-7 were isolated from embryos of germinating sugar beet seeds. B. pumilus isolates BMH5E-33 and BMH5E-40 were isolated from the sugar beet rhizosphere. All isolates were stored at −80'C in 10% glycerol and 1'% tryptic soy broth (Difco). For fresh cell preparations, the bacilli were cultured in tryptic soy broth for 48 hours at 28° C. Cells were centrifuged 15 min at 10,000 g (4° C.). washed with sterile water (2×), and resuspended in distilled water. The optical density was adjusted to $A_{600}=1.0$, and diluted 1:2 to obtain approximately $1 \times 10^8$ cfu/ml.

Fungal Culture

Cercospora beticola (CB) isolate EC3 (isolated in Sidney. Mont. in 1996) was grown on V-8 agar far a minimum of two weeks with exposure to fluorescent or natural light for at least one week to promote sporulation. Spores were harvested approximately 30 days. after plating in 0.1%, carboxymethylcellulose by scraping with a cotton swab, counted with a hemocytometer and adjusted to $1 \times 10^4$ spores/ml.

Disease Control Assays

Sugar beet cultivars Seedex 900012 and Holly Hybrid 88 in replicates of 10, were treated with a Bacillus mycoides strains, a Bacillus pumulus strain, acibenzolar-5-methyl (ASM, 50 ppm a.i. in distilled water. Actigard, 50 WG, Syngenta. Greensboro, N.C.) or distilled water with an aerosol sprayer to the leaf penultimate to the oldest true leaf. This leaf was then immediately bagged to ensure spatial separation from C. beticola, which was applied 3 days later at a rate of $1 \times 10^4$ spores/ml to near run-off on the remaining leaves using an aerosol sprayer. The sugar beets were kept at 28+/−2° C. and placed at 100% relative humidity for the first 48-72 hours, post-treatment. Plants were kept 28+/−2° C. until disease symptoms developed and were rated for disease at 21 days post-inoculation using the KWS scale, which rates percent disease severity on a scale of 0-9 (Kleinwanzler, 1970).

Results

Of the 14 different treatments applied to sugar beet cultivars Seedex 900012 and Holly Hybrid 88, four resulted in 50% disease reduction. The effective strains included BmJ, B. mojavensis isolate 203-7, and B. pumilus isolate 203-6 while the chemical inducer of systemic acquired resistance, ASM, also controlled disease. B. pumilus isolates 241-20-1 and 13MI-15E-40 reduced Cercospora leaf spot symptoms to a statistically significant level (Table 3) (Bargabus, et al., Biological Control, In Press (2004) herein incorporated by reference).

TABLE 3

Disease reduction capabilities of a pool of B. pumulis isolates, B. mycoides isolate BmJ, ASM, and water.

| | Disease severity at 21 days post challenge with C. beticola | |
|---|---|---|
| Treatment | HH88 | Seedex |
| water | 8.00[a] | 7.70[ab] |
| 203-3 | 5.82[a] | 5.58[b] |
| 203-4 | 6.95[a] | 7.65[ab] |
| 203-6 | 1.86[b] | 1.50[c] |
| 203-7 | 2.38[b] | 2.46[c] |
| 203-11 | 7.10[a] | 5.90[b] |
| BMH5E-33 | 6.42[a] | 6.60[b] |
| BMH5E-40 | 5.14[ab] | 5.45[bc] |
| 341-20-14 | 5.86[a] | 9.00[a] |
| 341-20-15 | 6.10[a] | 6.48[b] |
| 241-20-1 | 5.28[ab] | 4.66[bc] |
| 341-16-5 | 6.51[a] | 6.40[ab] |
| BmJ | 2.73[b] | 2.56[c] |
| ASM | 2.93[b] | 2.70[c] |

Example 5

Determining Induction of Systemic Acquired Resistance in Plants by Presence of Chitinase Protein Extraction For protein extractions, leaves distal to the treated leaves were collected from plants at 6 days post treatment with the live and dead BmJ, ASM, or water. One leaf per replicate was collected for each treatment and immediately placed in buffer (150 mm NaCl, 25 mm MES, pH 6-2). Apoplast extractions were collected as described by Klement [21] having substituted buffer (150 mM NaCl, 25 mm MES. pH 6 2) for water.

Western Analysis of Apoplastic Proteins

Apoplast samples were acetone precipitated (3:1 v/v), boiled in SDS sample buffer for 2 min, and resolved (1 5 ug per lane) (12% SDS-polyacrylamide gel electrophoresis (PAGE) gel) for 45 min (200 V) at pH 8.3 using midrange molecular standards (Sigma) for molecular weight determination. Proteins were then transferred to polyvinylidene fluoride membranes (Millipore) for 1 hour (100 V) in 25 mm Tris, 192 mm glycine, and 20% (v/v) methanol (pH 8.3) using a BioRad mini-blot apparatus [13]. Membranes were blocked with 3% BSA for 1 hour, incubated in primary antibody (anti-chitinase, diluted 1:5000) (Syngenta, Greensboro, N.C., U.S.A.) in 1 BSA for 1 hour, followed by incubation in secondary antibody (peroxidase conjugated, diluted 1:10 000) (Sigma). Colorimetric detection was performed using the 3-amino-9-ethylcarbazole (AEC) staining kit (Sigma). Loading equality was demonstrated with silver staining [26].

Determination of Chitinase Activity Following Non-reducing PAGE

Apoplastic protein samples (1.5 ug per lane) were resolved on a 12% polyacrylamide gel containing 0.01% glycol chitin. Following electrophoresis, the gel was gently shaken for 2 h (3rC) in 100 mM sodium acetate buffer, pH 5.0 containing 1% (v/v) triton X-100. The gel was then stained with 0.01% calcofluor white M2R in 500 mm Tris-HCl, pH 8.9 for 5 min. The gel was quickly rinsed 3× with distilled water, then soaked overnight in the dark in distilled water. Chitinase isoforms were visualized as lytic bands under an uv light source [50]. Size comparisons were made between active isoforms and isoforms detected by western analysis using mid-range molecular markers (Sigma).

Chitinase Specific Activity Determination by Plate Assay

Sodium phosphate buffer (pH 5.0, 0.01 M) containing 1 agarose and 0.1% glycol chitin was added to a 9 cm diameter glass petri dish. Wells, 3 mm diameter, were excised from the agarose (three per sample for each of the three replicates per treatment). Dilutions of apoplastic protein (0.7, 0.35, and 0.23 ug) and chitinase standards (chitinase from Streptomycesgriseus Sigma) were loaded into the wells. The plate was incubated at 37° C. for 24 h. Following the incubation, 50 ml of 500 mM Tris-HCl (pH 8.9) containing 0.01% fluorescent brightener was added to the plate and incubated for 10 min. The plate was then quickly rinsed 3× with water, flooded with water, and destained overnight in the dark. Non-fluorescent lytic regions on a fluorescent background were measured while the plate was on an uv light source. Specific activity (mg of N-acetyl-n-glucosamine released/hr/mg of apoplastic protein) was determined by comparison of the diameters of the lytic regions for the standards and the lytic regions for the apoplastic protein samples [55].

Results

Analysis of PR-protein production was used to help evaluate the hypothesis that BmJ induced systemic acquired resistance to CB. A protein extract from leaves distal to the treated leaves was prepared as described above. A polyclonal antibody to tobacco chitinase (provided by Syngenta, Greensboro, N.C.) bound to several putative chitinases in sugar beet following treatment with BmJ, ASM and water. As a means of determining which isoforms were potentially involved in sugar beet defense responses, the activity of the isoforms was observed following non-reducing PAGE. Certain isoforms showed increased activity while others appeared to have reduced activity in sugar beet following BmJ-treatment. There was equal loading in the PAGE analyses, as demonstrated when the apoplastic protein samples were also run on a separate polyacrylamide gel, then silver stained. One of the isoforms produced in response to BmJ-treatment, but lacking in the water-treated plants, was also found following ASM treatment, which is known to induce plant systemic resistance responses. The overall changes in specific activity of chitinase in sugar beet following treatment with ASM, live and dead BmJ and water were determined. Even though ASM-treatment resulted in fewer active isoforms being produced than the BmJ-treatment, the specific activity level was statistically equal (Table 4). Both live BmJ and ASM treatments resulted in statistically higher chitinase specific activity that was nearly twice that observed with water or dead BmJ treatment (Table 4).

TABLE 4

Systemic sugar beet apoplastic pathogenesis-related protein activity six days post treatment with line and dead *B. mycoides* isolate BmJ, acibenzolar-S-methyl and water

| Treatment | Specific Activity | | |
|---|---|---|---|
| | Chitinase[a] | Beta-glycanase[b] | Peroxidase[c] |
| Water | 0.46 | 36.1 | 42.8 |
| Live *B. mycoides* | 1.02 | 77.9 | 61.6 |
| Acibenzolar-S-methyl | 1.26 | 198.6 | 71.4 |
| Dead *B. mycoides* | 0.45 | 37.7 | 26.8 |
| LSD (0.05)[d] | 0.21 | 36.1 | 12.2 |

[a]Chitinase specific activity expressed as milligrams of .N-acetyl-n-glucosamine released per hour per milligram of apoplastic protein and is the mean of the data from three plants per treatment replicated three times.

[b]Beta-glucanase specific activity expressed as micrograms of glucose released per minute per milligram of apoplastic protein and is the mean of three plants per treatment replicate three times.

[c]peroxidase specific activity expressed as the changes in absorbance (470 nm) per minute per milligram of apoplastic protein and is the mean of three plants per treatment replicated three times.

[d]LSD = least significant difference (probability = 0.05).

Example 6

Determining Induction of Systemic Acquired Resistance in Plants by Presence of β-1,3-glucanase Detection of B-1.3-glucanase Activity Apoplastic proteins for each treatment (3.0 ug) were separated using acidic PAGE conditions as described by Reisfeld et al [39], with the following modification. In the running buffer, L-alanine was substituted for B-alanine with a final pH of 3.8 rather than the prescribed 4.3, allowing for better separation of the isoforms. Following separation, the gels were incubated in 0.1 M citrate buffer (pH 4.8) containing 250 mg laminarin per 100 ml of buffer at room temperature for 20 min. The gels were then transferred to 0.1% Congo red and incubated overnight with constant shaking at room temperature. The gels were then transferred to destaining solution (1 M NaOH) and incubated overnight at room temperature with constant shaking. B-glucanase activity was visualized as yellow-orange bands on a reddish-purple background.

Determination of β1-1,3-glucanase Specific Activity

The specific activity of sugar beet apoplastic β-1,3-glucanase was determined by measuring the release of glucose units from laminarin. Sodium acetate buffer (100 µl, pH 5.0, 100 mM) containing 0.5% laminarin and 0.5 ug-2.0 ug apoplastic protein (plants per treatment replicated 3 times) was incubated at 3rc for 30-60 min. Following incubation, 900 µl of water and 1 ml of alkaline copper reagent [45] was added to each 2 reaction. The tubes were then placed into a boiling water' bath for 10 min. After cooling on ice, 1 ml arsenomolybdate color reagent [33] was added to each reaction. Once the bubbling had subsided, 10 ml of water were added to each tube before reading the A660. A standard curve was established by adding 5 ug-25 ug glucose to 1 ml total reactions that did not contain laminarin.

Results

Native polyacrylamide gel electrophoresis (PAGE) was run under acidic conditions to examine basic β-1,3-glucanases produced in response to ASM, BmJ or water treatment. Two active isoforms were produced in sugar beet following BmJ treatment. One of the two isoforms was also present and active in sugar beet following ASM-treatment, however both were lacking in water-treated plants. To determine the total activity of β-1,3-glucanase in sugarbeet, colorimetric assays were performed. BmJ-treated plants had a specific activity that was approximately twice that of the activity in water-treated plants, but approximately one-third the ASM-induced activity; both were statistically significant increases when compared to the water-treated and dead BmJ-controls (Table 4). Dead BmJ-treated plants had specific activities statistically equivalent to the water-treated controls (Table 4).

Example 7

Determining Induction of Systemic Acquired Resistance in Plants by Presence of Peroxidase Determination of Peroxidase activity Apoplastic peroxidase activity from three plants per ASM, BmJ and water treatment (3 replicates of each) was measured using guaiacol reagent according to Hammerschmidt et al [15]. The concentration of protein as adjusted to give a change in absorbance units greater than 0.100, but less than 0.200, per minute. Specific activity was expressed as the increase in absorbance (A470) over time (2 min) per mg of protein, as determined using Bradford reagent (BioRAD).

Determination of Peroxidase Activity Following Native-PAGE

Polyacrylamide gel electrophoresis was performed according to Reisfeld et al. [39]. Following electrophoresis, the gels were stained using a AEC staining kit (Sigma) for 16 hours while gently shaking in the dark. The gels were then rinsed with distilled water 3× for a total of 15 min to stop the reactions.

Results

Peroxidase is a PR-protein that can be measured using activity assays. BmJ treatment elicited significantly greater peroxidase activity in the apoplast of distal sugar beet leaves than water or dead BmJ treatment (Table 4). Peroxidase activity following BmJ treatment was also statistically equivalent to that elicited by ASM (positive control) treatment (Table 4). To determine if the increased activity noted in the chemical SAR-inducer and bacterial treatments-was due to plant production of new peroxidase isoforms, in-gel activity assays were performed. Both the ASM- and BmJ-treated plants had two additional active isoforms not detected in the negative (water) control. There were several other minor isoforms that present in the water controls as well.

Example 8

Methods of Screening for Bacillus Control Agents-detection of Chitinase and β-1,3-glucanase Activity Apoplastic Protein Extractions The leaf penultimate to the oldest true leaf was treated with one of the *Bacillus* strains. BmJ, ASM, or distilled water, in replicates of 3, with an aerosol sprayer, and immediately bagged. The plants were kept at 28+/−2° C. for 6 days at which time the apoplastic proteins were collected as described by Klement (1965), with the following modification: a buffer containing 150 mM NaCl and 25 mM MES, pH 6.2, was substituted for distilled water. The proteins were quantified by Bradford reagent (Bio-Red) using bovine serum albumin as standards and frozen at −80° C. until analyzed.

Glycol Chitin Plate Assay for Chitinase Activity

Apoplastic protein (0.009, 0.006, and 0.005 ug for each sample in replicates of 3) was added to wells in a 1% agarose gel containing 0.01% glycol chitin in a 14 cm diameter glass petri plate, along with chitinase standards (*Streptomyces griseus*, Sigma). The plates were incubated at 37° C. for 24 hours. Following incubation. 50 ml of 500 mM Tris-HCl (pH 8.9) containing 0.01°/fluorescent brightener [28] was added to the plate for 10 min. The plate was then rinsed three times with distilled water, flooded with water, and allowed to destain in the dark for 2-24 hours. The non-fluorescent lytic zones on a fluorescent background were measured while the plate was on a 302 nm UV light source. Specific activity (mg of N-acetyl-D-glucosamine released/hr/mg of apoplastic protein) was determined by comparison of the lyric zone diameter of the standards and the apoplastic samples (Velasquez. 2002).

Results-Chitinase as a Predictor of Disease Control

An increase in chitinase specific activity following treatment with a *Bacillus* control agent in comparison to the water-treated negative control constituted the classification of the agent as a SAR-inducer. The glycol chitin plate assays, for the determination of chitinase activity, had a reasonable level of precision with discrepancies having occurred only 9% of the time between independent experiments. The standard deviation within a subset in one independent replicate was approximately 10% and approximately 17% between subsets in one independent experiment.

Cumulative results of five independent experiments correctly identified all four SAR-inducers present in the pool of isolates tested and yielded four false positives and no false negative identifications (Table 5).

Aniline Blue Plate Assay for B-glucanase Activity

Apoplastic protein (0.75, 0.50, and 0.25 ug for each sample in replicates of 3) was added to 3-mm diameter wells in a 0.5% agarose gel containing 0.005% aniline blue (MCB) and 0.5 m.l/ml laminarin (from *Laminaria digitata*, Sigma) in a 14 cm diameter glass petri plate, along with laminarinase (*Penicillium* spp., Sigma) standards ($2\times10^{-5}$-$2\times10^{-3}$ units of lamina~inase). The plates were incubated at 30° C. for 18-24 hours. Following Incubation, the pink lytic zones on a blue background were measured while the plate was on a white light source. Specific activity (ug of glucose released/min/mg of apoplastic protein) was determined by comparison of the lytic zone diameter of the standards and the apoplastic samples.

Results-B-1,3-glucanase as a Predictor of Disease Control

An increase in B-1,3-glucanase specific activity following treatment with a Bacillus control agent in comparison to the water-treated negative control constituted the classification of the agent as a SAR-inducer. The aniline blue plate assay was highly reproducible with a standard deviations of 11% within subsets of one replication and 21% between subsets in one replication. There was a high degree of precision when using the aniline blue plate assay with few false positive identifications (0-40% between independent experiments) and no false negative identifications. Based on the increase in activity serving as an indicator of SAR induction, the cumulative results of two independent experiments yielded one false positive identification (Table 5).

Results-Chitinase and B-1,3-glucanase as a Predictor of Disease Control

There may be circumstances where the occurrence of chitinase and B-glucanase alone is not correlated with disease control (Punja, 2001), especially with fungal pathogens, since the enzymes function synergistically (Melchers and Stuiver, 2000). Therefore examination of the defense proteins together provides a more accurate prediction of disease control capability. Based on the assumption that increased activity for both defense proteins indicated SAR-inducing capacity, combined results from the glycol chitin and aniline blue plate assays correctly identified all SAR-inducing isolates, indicated by check marks in Table 5. Furthermore, relying on this method did not include any false-positive identification.

TABLE 5

Cummulative results of the methods for host-response based high-throughput screening for the identification of Bacillus control agents.

| Treatment | Aniline blue plates | Glycol chitin plates | Aniline blue and glycol chitin plates |
|---|---|---|---|
| water | 2.75cd | 1.56g | |
| 203-3 | 3.20cd | 2.55def | |
| 203-4 | 3.35bcd | 2.03fg | |
| 203-6 | 4.90ah | 2.97bcd | ✓ |
| 203-7 | 5.75a | 4.00a | ✓ |
| 203-11 | 4.00b | 2.04fg | |
| BMH5E-33 | 2.80cd | 2.1gefg | |
| BMH5E-40 | 2.35d | 2.22efg | |
| 341-20-14 | 3.85bcd | 2.68def | |
| 341-20-15 | 2.70cd | 2.14efg | |
| 241-20-1 | 2.55cd | 2.74cde | |
| 341-16-5 | 3.15cd | 3.44eb | |
| BmJ | 6.10a | 3.41 abc | ✓ |
| ASM | 5.70a | 3.09hed | ✓ |

Example 9

Methods of Screening for Bacillus Control Agents-detection of Biphasic Hydrogen Peroxide Production Sugar Beet Protoplast Generation Sugar beet protoplasts were isolated from sugar beet leaves to provide a medium to measure hydrogen peroxide production. Sugar beet leaves were gently brushed on the adaxial and abaxial surfaces with a 50 ft bristle brush to create small abrasions. The leaves were then cut into 1 cm strips and vacuum infiltrated for 5 min with 0.7 M sucrose containing 3.8% CaCL2, CPW salts (Frearson et al, 1973), 1.2% cellulase (Sigma), and 0.4% macerozyme (ICN Biomedicals). The infiltrated leaves were incubated in the 0.7M sucrose-salt and enzyme solution for 24-48 hours in the dark. Following incubation, the enzyme solution was gently removed and the protoplasts were released into 0.7M sucrose containing 3.8% CaCI2 and CPW salts by gently shaking the leaf strips in the solution. Phenol red oxidation for hydrogen peroxide production.

To determine if the Bacillus strains elicited biphasic hydrogen peroxide production in sugar beet, phenol red oxidation assays were performed according to Pick and Keisari (1980). Both protoplasts (250 protoplasts/reaction) and whole leaf disks (12 disks/reaction) were used to study the plant response. When using protoplasts, an external source of peroxidase (type 11 horseradish peroxidase, Sigma) was added to each reaction while in the latter case. The peroxidase contained within the added leaf disks was sufficient for the oxidation reaction. Phenol red reactions were run with each Bacillus strain alone, protoplasts alone, leaf disks alone, Bacillus-treated leaf disks, and combinations of Bacillus strains and protoplasts. Bacillus treated leaves were washed before adding to each reaction to remove a majority of the bacteria from the leaf surface. To calculate the amount of hydrogen peroxide produced in each instance, the A470 was compared to a standard curve established using 0-40 mM hydrogen peroxide and 6-2 ug/ml type II horseradish peroxidase. The amount of hydrogen peroxide produced from protoplasts in response to treatment with a Bacillus control agent was calculated as follows: amount of hydrogen peroxide produced in Bacillus protoplast reactions−(amount of hydrogen peroxide produced in protoplast only reactions+amount of hydrogen peroxide produced in Bacillus-only reaction). The amount of hydrogen peroxide produced by the leaf disks in response to Bacillus treatment was calculated as follows: amount of hydrogen peroxide produced by Bacillus-treated leaf disks-amount of hydrogen peroxide produced by leaf disks only reaction.

Results-Biphasic Hydrogen Peroxide Production Curves as Predictors of Disease Control Biphasic hydrogen peroxide production, as measured using phenol red oxidation, was used as an indicator of SAR-induction capability. In cases where a single burst of hydrogen peroxide occurred without the secondary, more prolonged AOS burst, the strain was classified as a non-SAR inducer. AOS production profiles were similar regardless of the plant material used to analyze the production pattern of hydrogen peroxide. The reproducibility was quite high with only 7% disagreement between independent experiments using protoplasts and leaf disks. All biphasic curves elicited by the Bacillus strains were statistically similar in timing and intensity. In all cases the primary peak (approximately 3 mM) occurred at 15 min post-treatment and the secondary peak (approximately 2-4 mM) occurred at approximately 2 hour post-treatment. False positive identification using this method occurred 8-15% of the time between independent experiments. ASM did not induce biphasic hydrogen peroxide production.

Example 10

Use of Bacillus Control Agent in Disease Control in Banana Plants

Spray-dried cells of Bacillus mycoides isolate J (BmJ) were prepared as described in Example 2. The spray-dried BmJ was applied aerially at a concentration of $1\times10^6$ cfu/ml at a rate of 7 gallons/acre to banana plants. The ability of the BmJ treatment to control the fungal disease Black Sigatoka (caused by Mycosphaerella fijiensis) was determined. The banana plants were infected by the pathogen Mycosphaerella

*fijiensis* present in the field under naturally occurring conditions. Efficacy of BmJ treatments were evaluated in comparison with the fungicides TPTH at 5 oz per acre and Propaconizole at 10 oz per acre. These rates are the recommended application rates for these fungicides. Results were assessed by visual scoring of leaf tissue damage.

Results

Treatment of the banana plants with BmJ was just as effective at controlling Black Sigatoka as treatment of banana plants with the fungicide TPTH.

Example 11

Use of *Bacillus* Control Agent in Disease Control in Pecan Plants

Spray-dried cells of *Bacillus mycoides* isolate J (BmJ) were prepared as described in Example 2. The spray-dried BmJ was applied by an orchard spray mechanism at a concentration of $1 \times 10^6$ cfu/ml at a rate of 200 gallons/acre to pecan plants. The ability of the BmJ treatment to control the fungal disease Pecan scab (caused by *Cladosporium caryigenwn*) was determined. The pecan trees were infected under naturally occurring conditions by the pathogen *Cladosporium caryigenum* present in the orchard. BmJ treatments were compared with the fungicide TPTH applied at the recommended rate of 5 oz per acre. Disease damage was rated by visual observation using a numerical scale.

Results

Treatment of the pecan plants with BmJ was just as effective at controlling Pecan scab as treatment of pecan plants with the fungicideTPTH.

Example 12

Use of *Bacillus* Control Agent in Disease Control in Cucumber Plants

The anthracnose and angular leaf spot-cucumber-pathosystems were used to compare disease control using induced systemic resistance by *Bacillus mycoides*, isolate BmJ and *Bacillus mojavensis*, isolate MSU 203-7.

Bacilli were applied as a first true leaf treatment at $10^9$ colony forming units (cfu)/ml 5 days before challenge inoculation with *G. cingulata*=$10^5$ conidia/ml and *P. syringae*=$10^4$ cfu/ml. Five days (seven days for the angular leaf spot-pathosystem) after challenge inoculation, disease development was compared to water treated and pathogen-induced controls. BmJ treatments significantly lengthened the latent period by approximately 1 day and decreased both total spore production by approximately 64% and the percentage of viable spores by approximately 54% in the anthracnose experiment. The percent of infected leaf area was significantly reduced by approximately 37% and 48% by *B. mycoides* and *B. pumilus*. Both *Bacillus* treatments also reduced the systemic movement by approximately 27% and 36% in the angular leaf spot experiment.

Example 13

Determining Impact of SA and NPR1 Signaling on Induction of Systemic Acquired Resistance in Sugar Beets Plants have a variety of means of defending themselves against pathogen attack. Some constitutive lines of defense include physical barriers that prevent pathogen ingress and can contain antimicrobial proteins and secondary metabolites (reviewed by Vorwork et al, 2004) and production of toxins that are deleterious to particular pathogens (reviewed by Wittstock and Gershenzon, 2002). Additionally, in some instances, plants can mount an inducible defense response upon pathogen challenge. Inducible broad-spectrum resistance provides long-term defense against a wide array of potential pathogens and has been described in several plant systems in response to a variety of different stimuli (Ryals et al, 1996; van Wees et al, 1997; Yoshioka et al, 2001, Yasuda et al, 2003).

Signaling components involved in elicitation of defense are largely unknown. However, several key players have been identified, such as salicylic acid ("SA") (Ollestam and Larsson, 2003; Shah, 2003; Alvarez, 2000; Shapiro and Gutsche, 2003), jasmonic acid (JA) and ethylene (Heil and Bostock, 2002, Anderson et al, 2004), all of which are considered secondary signal molecules. Some downstream signaling components, such as NON-EXPRESSOR OF PATHOGENESIS-RELATED GENES1 (NPR1) have been shown to be deployed during SA-dependent defense (reviewed by Dong, 2004). NPR1 has also been shown to orchestrate cross-talk between SA and JA pathways (Spoel et al, 2003). These antagonistic pathways elicit distinct subsets of defense-related proteins. SA-dependent pathways are associated with pathogenesis-related (PR) proteins such as chitinase, peroxidase, glucanase and PR-1 (reviewed by Durrant and Dong, 2004). JA and ethylene, on the other hand, are associated with production of thionins, defensins and proteinase inhibitors (Reymond et al, 2000; Xu et al, 2001).

SA is tied to the oxidative burst, one of the earliest events in the establishment of induced resistance. Interaction occurs between SA and active oxygen species (AOS) produced during the oxidative burst. SA can bind to and inhibit antioxidant enzymes leading to an increase in AOS concentration (Chen et al, 1993; Durner and Klessig, 1995). Additionally, hydrogen peroxide, one of the AOS, has been shown to be involved in the potentiation of phenylalanine ammonia lyase and benzoic acid 2-hydroxylase (Leon et al, 1995); two enzymes in one of the SA biosynthetic pathways (Coquoz et al, 1998). It has also been hypothesized that AOS may be involved in the liberation of free SA from elusive SA conjugates constitutively stored in plant cells (Leon et al, 1995).

SA and AOS are also linked to activation of NPR1, a protein that functions downstream of SA signaling. NPR1 is a constitutively expressed protein that contains domains which function in protein-protein interactions (Cao et al, 1997; Aravind and Koonin, 1999). The protein exists in an inactive multimeric state. Increased concentrations of AOS during the oxidative burst triggers overproduction of antioxidant enzymes in the plant. The AOS scavenging is hypothesized to create the reducing environment necessary to release an active monomer of NPR1 (Mou et al, 2003). The monomeric NPR1 moves to the nucleus, associates with TGA transcription factors and activates PR-genes (Fan and Dong, 2002).

Previously we have described the biochemical outcome of treatment of sugar beet with two biological control agents (BCA), *Bacillus mycoides* isolate Bac J (BmJ) (Bargabus et al, 2002) and *Bacillus mojavensis* (previously identified as *B. pumulis*) isolate 203-7 (203-7) (Bargabus et al, 2004). Both biological control agents induce resistance that affords protection against *Cercospora beticola*, the causal agent of *Cercospora* leaf spot, a devastating foliar pathogen of sugar beet (Weiland and Koch, 2004). Since the resistance is associated with production of SA-associated PR-proteins (peroxidase, 13-glucanase and chitinase), we have hypothesized the signaling pathway is SA dependent. Due to the fact both BCAs elicit an oxidative burst (Bargabus et al, 2003 and 2004), we have speculated that NPR1 may also be deployed in the establishment of resistance. In the current investigation we test these hypotheses to determine the role of SA and NPR1 in Bacilli-induced resistance in sugar beet.

Plant Culture

Beta vulgaris FC 607 germplasm (provided by Dr. Lee Panella, United States Department of Agriculture-Agricultural Research Service, Fort Collins, Colo.) was seeded into 20-cm diameter pots containing pasteurized Scotts Metro-Mix supplemented with Scotts Osmocote 14-14-14 (American Clay, Denver, Colo.). Seed was dusted with a 4:1(v/v) charcoallmetalaxyl (Apron, Gustafson, Plano, Tex.) mixture prior to planting to control damping off by Pythium. Plants were maintained at 22° C.±5° C. and were watered twice a week to maintain vigorous growth. At about four weeks, Imidacloprid (Marathon, 1% granular, ½ tsp/pot) and triazole (Strike, foliar spray, 1.9 g/l) (Olympic Horticultural Products Co., Mainland, Pa.) were used as preventatives for thriplaphid feeding and powdery mildew respectively. Plants used in all experiments were between 5 and 7 weeks of age. The photoperiod of light was determined by natural sunlight of 12 to 15 hours.

Bacterial Cultures

Bacillus mycoides isolate Bac J (BmJ), originally isolated from sugar beet leaves in Sidney, Mont. in 1994, was prepared as previously described (Bargabus et al, 2002). Bacillus mojavensis isolate 203-7, originally isolated from embryos of germinating sugar beet seed in 1997, was prepared as previously described (Bargabus et al, 2004). Bacillus pumulis isolate BMHSE-33, originally isolated from the sugar beet rhizosphere in Sidney, Mont. in 1'997, was prepared as previously described (Bargabus et al, 2004). Treatment of Sugar Beet with Elicitors of Systemic Resistance [0114] Acibenzolar-5-methyl (ASM, 50 ppm a.i.; Actigard 50WG, Syngenta, Greensboro, N.C.), a known chemical of inducer of resistance, was applied as an experimental control for SA and NPR1 analysis. ASM and live and autoclave killed (dead), washed BmJ, 203-7 and BMHSE-33 cells were spray applied to near run off to all fully expanded leaves. Water was spray applied as an experimental negative control for all treatments. In NPR1 experiments, SA (2 mM in 0.1M potassium phosphate buffer, pH 7.0, containing 0.01% triton x-100) was added as an additional positive control. Extraction of Free and Conjugated Salicylic Acid from Sugar Beet Leaf Tissue.

Two main precursors, isochorismate (Wildermuth et al, 2001) and phenylalanine (Ribnicky et al, 1998), are implicated in the formation of SA during plant defense, both of which stem from the shikimic acid pathway (Metraux, 2002). Salicylic acid is produced locally in treated leaves and systemically in distal, untreated leaves during the establishment of systemic acquired resistance. Production is transient and free SA is rapidly modified to 2-0-b-D-glucosylsalicylic acid (Enyedi and Raskin, 1993), a hypothetical SA storage compound. Therefore the best measure of SA-dependency is gathered by measuring free and conjugated SA, or total SA, concentrations over time.

One half of each treated leaf was excised and weighed (one leaf half per plant; two plants per time point). Sampling was conducted over a 48 hour timeline (0, 1, 3, 6, 8, 24, 30 and 48 hours). The free and conjugated (2-o-β-D-glucosylsalicylic acid) SA was extracted as described by Verberne et al (2002) with the following modifications. Instead of being ground in liquid nitrogen, fresh leaf samples were ground directly in methanol using a glass tissue macerator. Additionally, the samples were dried by blow down under air, instead of in a SpeedVac (company, location) concentrator. These experiments were repeated on three independent occasions.

High Pressure Liquid Chromatography Determination of Salicylic Acid Concentration Dry samples were dissolved in absolute methanol (0.5 ml) and filtered through a 0.45 µm nylon filter (Supelco, Bellefonte, PAL Acetic acid (0.5 ml of 1.2% v/v) was added and the sample was filtered a second time using a 0.45 µm nylon filter. Sample (50 µl) was injected onto a Supercosil LC-18 HPLC column (250×4.6 mm, Sigma, St. Louis, Mo.) equipped with a C-18 guard column (7.5×4.6 mm, Alltech, Deerfield, Ill.). Elution was isocratic using 1:1 methanol to 1.2% v/v aqueous acetic acid at 0.8 ml/min. Under these conditions, SA had a retention time of 9.6 min at room temperature. Detection was performed using a Model L-4500A diode array detector (Hitachi, Tokyo, Japan). Integration of the salicylic acid peak was performed at 240 nm. A standard curve was developed based on integration values of salicylic acid in 1:1 methanol to 1.2% aqueous acetic acid (0.25-10.0 ug/ml).

Determination of Percent Recovery for Salicylic Acid

To determine the amount of salicylic acid lost during extraction, several untreated leaf samples (2/SA concentration) were spiked with SA (0, 10, 100 and 200 mg) dissolved in 100% methanol. The samples were ground and SA was extracted as described above. The percent of recoverable SA was determined by comparing the integration values obtained by HPLC to a standard curve developed for SA. The experiment was repeated on two independent occasions.

Protein Extraction and Electrophoresis

To examine activation of NPR1, total protein was extracted from sugar beet leaf tissue at 2 days post treatment with ASM, live and dead BmJ, 203-7, BMH5E-33, SA and water using a plant fractionated protein extraction kit (Sigma, St. Louis, Mo.) according to the manufacturer's recommendations. Additionally, total protein was extracted from Live BmJ-treated tissue over an expanded 48 hour timeline (0, 0.5, 3, 6, 8, 24, and 48 hours). Protein concentration was determined by Bradford assay (BioRad) in comparison with bovine serum albumin standards (0-20 mM). Proteins (100 mg/sample) were heated to 60° C. for 10 min in sample loading buffer (125 mM Tris-HCl, pH 6.8, 5% SDS, 25% glycerol and 0.4% bromphenol blue). When the samples were to be reduced, 50 mM Dithiothreitol (DTT) was added to the sample loading buffer. Proteins were resolved (12% SDS-polyacrylamide gel electrophoresis (PAGE) gel) for 45 min (200 V) at pH 8.3 using molecular standards (BioRAD) for molecular weight determination. Both sets of experiments were replicated three independent times.

Western Analysis

Following electrophoresis, proteins were transferred to polyvinylidene fluoride membranes (BioRad) for 1 hour (100 V) in 25 mM Tris, 192 mM glycine and 20% (v/v) methanol (pH 8.3) using a BioRad mini-blot apparatus according to the manufacturer's recommendations. Membranes were blocked with 3% BSA for 1 hour, incubated in primary anti-Arabidopsis NPR1 antibody (Provided by Dr. Xinnian Dong, Duke University, Durham, N.C.; Mou et al, 2003, diluted 1:15,000) overnight at 4° C., followed by incubation in peroxidase-conjugated goat-anti-rabbit secondary antibody (BioRad, diluted 1:10,000) for 1 hour at room temperature. Colorimetric detection was performed using the 3-amino-9-ethylcarbazole (AEC) staining kit (Sigma, St. Louis, Mo.).

Results-Salicylic Acid

BmJ and 203-7 both elicit systemic resistance independent of SA accumulation. Over a 48 hour sampling scheme no statistical increases were noted between total SA levels at time zero and other time points in the Bacilli-treated leaves.

The trend for SA levels was the same for water- and BMH5E-33-treated leaves. As shown in FIG. 1, at several later time points (6, 8, 30 and 48 hours post treatment), 203-7-treated leaves had a statistically significant decrease in SA levels.

Figure 2:
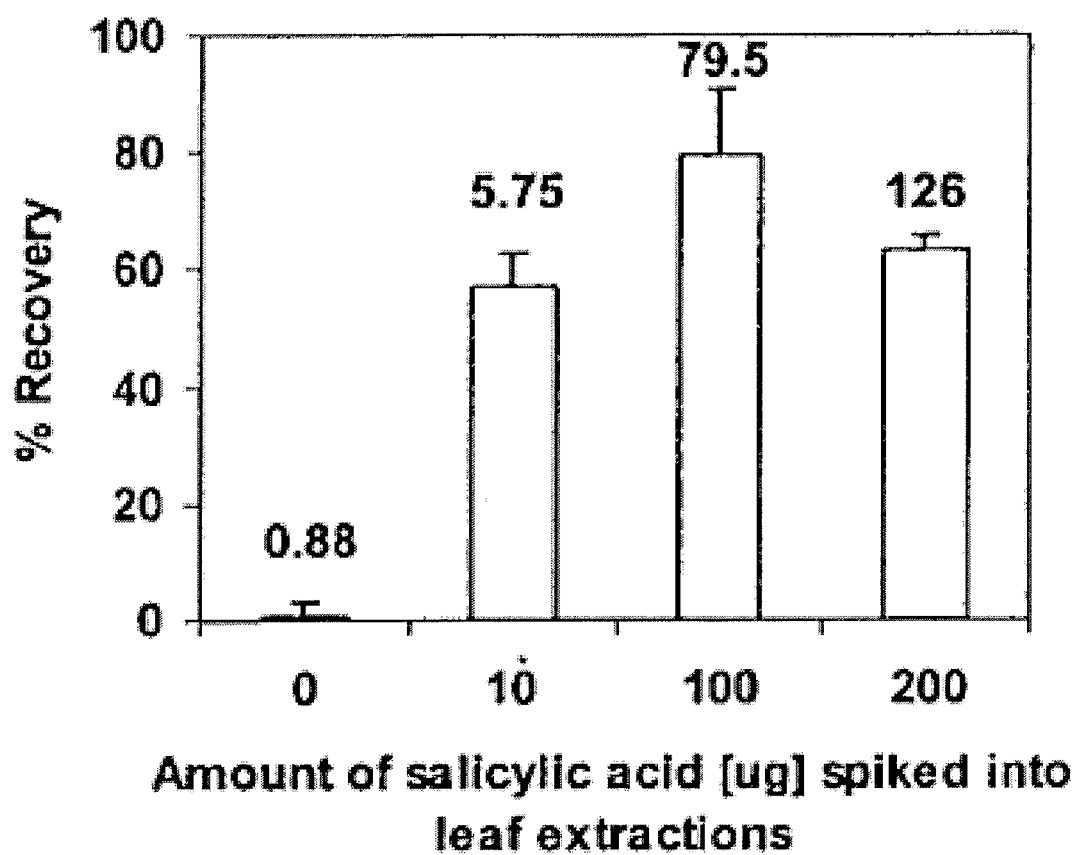
FIG. 2 depicts a graphic representation relating to the amount of recoverable salicylic acid after extraction, thereby indicating the amount of salicylic acid lost during extraction, according to one embodiment of the present invention.

Determination of Percent Recovery for Salicylic Acid. Salicylic acid extraction methods provide notoriously poor recovery rates. Therefore, it was important to determine the amount of SA lost during the current extraction procedure. In the current experiment, recovery of spiked SA ranged from 57 to 79 percent. As seen with the unspiked samples, the total SA level is not at zero under basal conditions as shown in FIG. 2.
Results-NPR1

Figure 3:
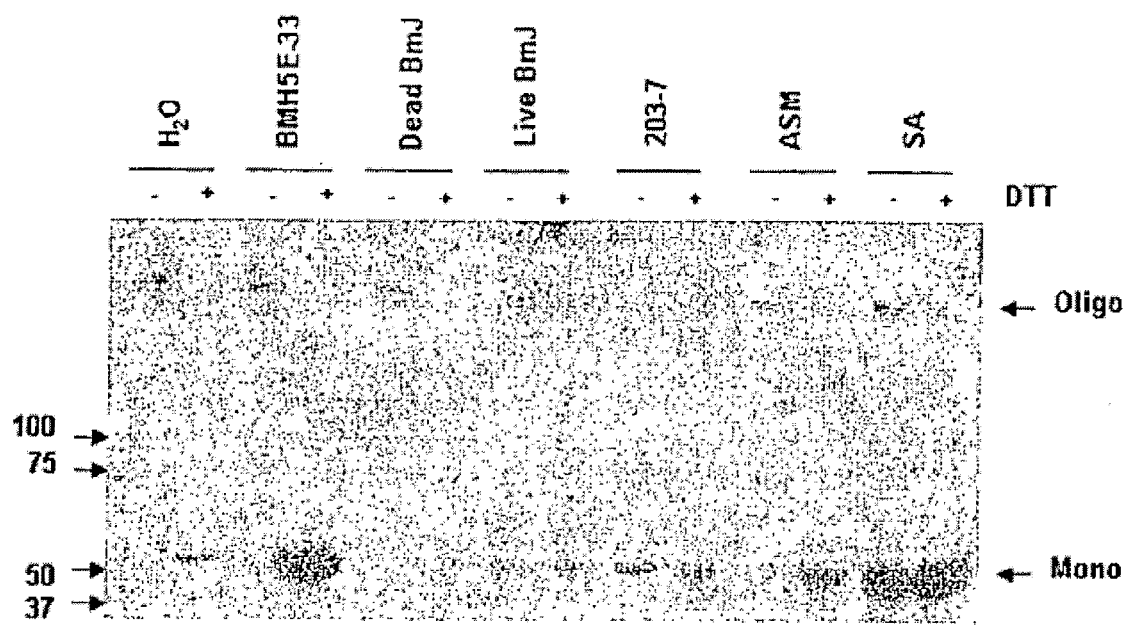
FIG. 3 depicts a graphic representation of the relationship between the addition of various agents and the activation of NPR1, according to one embodiment of the present invention.

Only the inducers of resistance, live BmJ, 203-7, SA and ASM, activated NPR1 by 48 hours. Our negative controls, water and BMH5E-33, did not elicit reduction of the NPR1 oligomeric complex. However, it is shown in FIG. 3 that the NPR1 monomer could be "forcibly" released through addition of OTT, a reducing agent, in the loading buffer. When examining NPR1 activation following BmJ treatment over an expanded timeline, the monomeric form was first detectable at 3 hours post treatment and remained active through 48 hours of sampling.

Prior accounts have shown NPR1 is activated early in plant defense and remains active at least through 48 hours post elicitation, therefore NPR1 monomerization was examined at 2 days post treatment with live and dead BmJ, ASM, 203-7, BMH5E-33, SA and water.
Discussion Summary. Both BCAs elicit systemic resistance independent of SA accumulation, since there was no statistical increase in SA level in sugar beet leaf tissue over a 48 hour timeline following treatment with BmJ or 203-7. Additionally, the SA trend over time was similar to that observed following water and *Bacillus pumulis* isolate BMH5E-33 (BM145E-33) treatment, an experimental and biological negative control respectively.

This would indicate the involvement of a novel secondary signaling component or activation of the signal transduction cascade downstream of SA accumulation. The latter is similar to acibenzolar-5-methyl activation of sugar beet systemic resistance which is SA-independent but NPR1-dependent. Without being limited by theory, we initially thought that both BmJ and 203-7 BCAs may activate NPR1, a protein associated with transcriptional activation of pathogensis-related genes. NPR1 was activated by 3 hours post treatment with BmJ in expanded sampling timelines. This timing of activation corresponds to the conclusion of the secondary hydrogen peroxide burst elicited by BmJ. The information obtained in this current investigation has allowed for further development of a working model for understanding signaling in BmJ- and 203-7-induced resistance in sugar beet.

No SA Accumulation. Surprisingly, SA accumulation in sugar beet following BCA treatment was absent. As shown in FIG. 2, there was no statistical difference in SA level over time following BmJ treatment and the overall trend for SA was similar to that following water or BMH5E-33 treatment, both of which are negative controls.

Salicylic acid levels in SA-dependent resistance have been reported to rise as much as 15-fold over the basal level following resistance elicitation. Without being limited by theory, it is unlikely the current extraction or detection method are responsible for a failure to uncover a response of this magnitude, especially when we have observed 57-79% recovery of free SA spiked into samples prior to extraction, as shown in FIG. 1. Additionally, when testing for SA accumulation in sugar beet using a chemical positive control that activates SAR upstream of SA (probenazole, Yoshioka et al, 2001), there was a trend towards increased total SA levels over time (data not shown).

Interestingly, 203-7 treatment, which elicits similar biochemical responses from beet as BmJ, alternately led to a statistically significant decrease in SA levels over time, as shown in FIG. 2. However we do not consider this to be of biological significance since the change is so nominal.

Acibenzolar-5-methyl ("ASM"), a functional analog of SA (Tally et al, 1999; Lawton et al, 1996), activates the signal transduction cascade downstream of SA production which has been demonstrated using nahG plants (Chandra-Shekara et al, 2004). Therefore, the lack of SA accumulation following ASM application was expected.

NPR1 likely has role in SeA-induced resistance. Both BCAs in this study elicit an oxidative burst and PR-protein production in sugar beet, the activator and result of NPR1 monomerization respectively. Therefore a role for NPR1 in BCA-induced resistance seems likely. Other reports have shown NPR1 is activated early in plant defense and remains active through 48 hours post treatment (Mou et al, 2003) All of our inducing treatments, SA, ASM, live BmJ and 203-7, activated NPR1 by 2 days post application. On the other hand, water, dead BmJ and BMH5E-33, non-inducers, did not activate NPR1 at the time points examined, as seen in FIG. 3. None of the plants had any monomeric NPR1 present at time zero, which immediately proceeded application of our various treatments (data not shown). The antibody used in this study detected both the oligo- and monomeric forms of the protein. Live BmJ, ASM, SA and 203-7 treatment lead to partial reduction of the protein complex. Addition of on, a reducing agent, fully reduced the oligomer. Furthermore, the multimer of NPR1 was detected in the water-, dead BmJ- and BMH5E-33-treated samples, as would be expected of a constitutively expressed protein. Addition of on, in these cases as well, lead to full reduction of NPR1 into a monomeric state. Interestingly, in *Arabidopsis* this particular antibody only detects monomeric NPR1 (Mou et al, 2003).

Without being limited by theory, we initially thought that Bacilli BCA-induced resistance appears to be SA-independent but NPR1-dependent leads to two hypotheses: 1) Bacilli-induced resistance activates the SA-dependent signaling cascade downstream of SA, or 2) SAR is activated through reliance on a novel signaling compound. The former is similar to what is observed with several chemical inducers, such as ASM, 2,6-dichloroisonicotinic acid (Nakashita et al, 2002) and N-cyanomethyl-2-chloroisonicotinamide (yasuda et al, 2003). Salicylic acid does not directly activate NPR1; activation is achieved through an intermediate. Since NPR1 is activated by 3 hours following BmJ treatment, which corresponds to the peak of the secondary oxidative burst (Bargabus et al, 2003), this intermediate factor may be activated through peripheral OXB-associated responses, bypassing the need for SA accumulation.

Pathogenesis-related proteins induced by BmJ and 203-7 are associated with a typical SA-reliant pathway which is antagonistic towards JA-dependent defense (Felton and Korth, 2000; Gupta et al, 2000). Therefore, without being limited by theory, we initially thought that a novel signal, other than JA-ethylene, seems more likely deployed by these BCAs based on the Example 13. Other accounts of signaling components associated with Bacilli-induced resistance do not reach a congruent conclusion. Ryu et al (2004a) showed an isolate of *Bacillus pumulis* induced SA-independent resistance in *Arabidopsis* effective against Cucumber mosaic virus. Another BCA in the study, *Serattia marcescens*, activated a JA-dependent NPR1-independent pathway. However,

*B. pumulis* dependence on JA and NPR1 was not discussed. In a separate study, Ryu et al (2004b) showed that an isolate of *Bacillus subtilis* induced systemic resistance through ethylene-dependent pathways completely independent of both SA and JA. Yet another isolate of *B. subtilis*, when tested on cucumber and tomato, induced resistance associated with differential accumulation of plant transcripts distinct from classical SA or JA associated SAR markers (Ongena et al, 2004). Again without being limited by theory, perhaps this is evidence of a novel BCA signaling cascade and defense response. Adding to the complexity, *B. amyloliquefaciens* induced NPR1-dependent resistance associated with both SA- and JA-dependent defenses (Anh et al, 2002). Interestingly, in pathogen-elicited defense, NPR1, when triggered through SA-dependent channels, represses JA-associated protein production (Spoel et al, 2003). This demonstrates that BCA activation of NPR1 has a different outcome altogether than pathogen activation, which may suggest involvement of novel signaling component. Whether BmJ and/or 203-7 elicit production of jasmonate-associated proteins has not been investigated based on the presumed universal antagonism between SA and JA. The fact that some BCAs are able to concordantly induce these normally inhibitory pathways provides additional credence to the idea that a unique signal is being produced that does not impart negative regulation on either subset of JA or SA associated genes.

Figure 4:
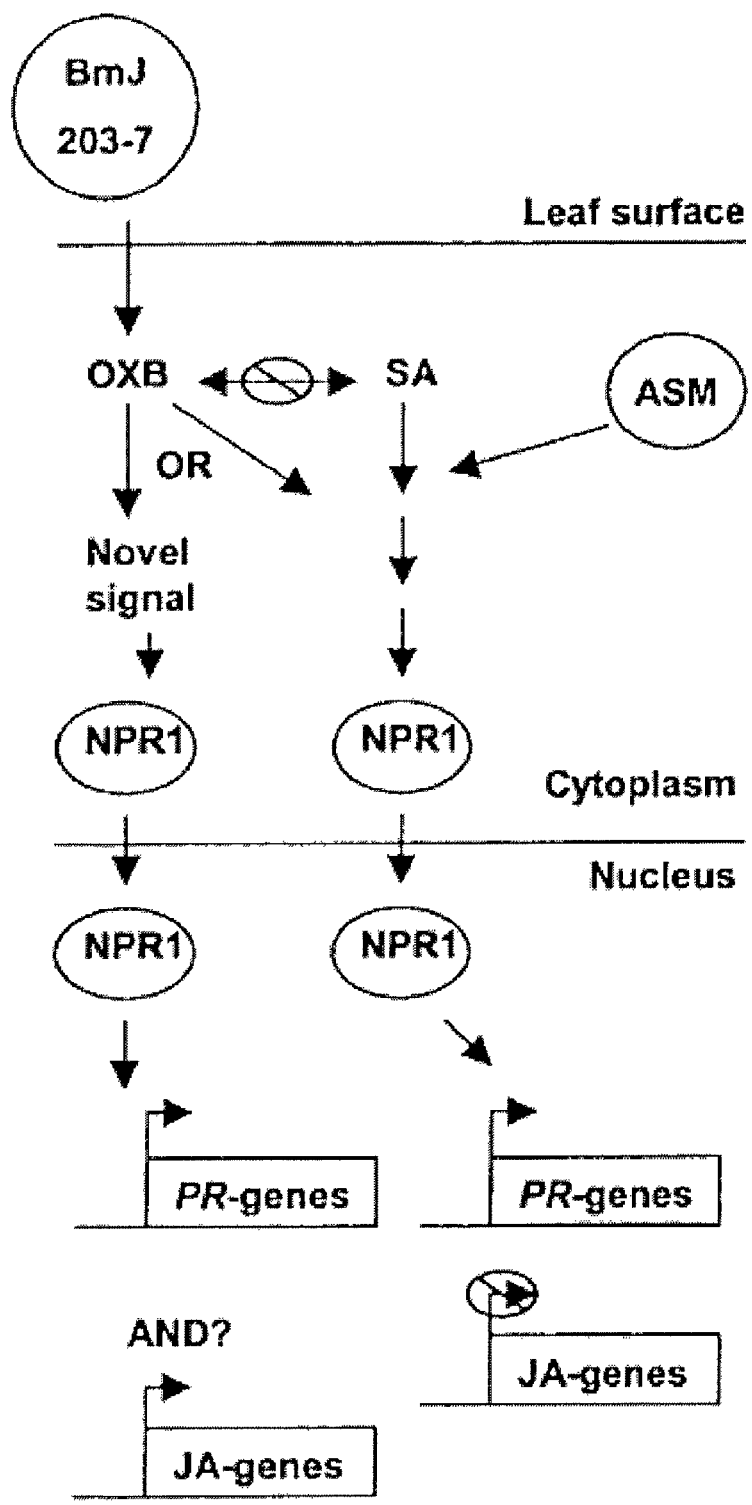
FIG. 4 depicts a schematic representation of a BCA-sugar beet interaction model, in accordance with one aspect of the present invention.

The information gathered in this current investigation has allowed for further expansion of our BCA-sugar beet interaction model, as shown in FIG. 4.

Example 14

Defense Pathways Activated by *Bacillus mojavensis* Isolate 203-7 and *B. mycoides* Isolate BmJ as Elucidated by *Arabidopsis* Mutants Bacterial Cultures:
*B. mycoides* isolate BmJ (BmJ) was originally isolated from sugar beet leaves. *B. mojavensis* isolate 203-7 (203-7) originally isolated from sugar beet seed embryos was included in the greenhouse experiments since it showed good induction of SAR in previous experiments (Bargabus et al., 2004). Bacteria were cultured in 3% TSB for 24 hr at 22° C. on an orbital shaker at 250 rpm. Fresh cells were harvested by centrifugation for 20 min at 5,000 rpm at 4° C. The pellet was re-suspended in sterile-distilled water and pelleted twice by centrifugation for 20 min at 5,000 rpm at 4° C. to assure that all fermentation beer was separated from the cells. The inoculum density was adjusted to $10^8$ colony forming units (CFU)/ml with distilled water and was applied using an aerosol sprayer with applications made to run-off.

Fungal culture:

*Botrytis cinerea* isolate Bot-I was originally isolated from infected plant material and conidia were stored at −80° C. Conidia were streaked onto 50% potato dextrose agar using a sterile loop and incubated at 24° C. for 2 weeks. Plates were flooded with a solution consisting of 6.2 mM KH2P04 and 5.5 mM glucose in sterile-distilled water and conidia were loosen with a sterile glass rod. Conidia suspension was decanted and filtered through two layers of cheesecloth to remove mycelium and agar pieces. The inoculum density was adjusted to 105 conidia/ml.

*Arabidopsis thaliana* Wild Type and Mutants:

*Arabidopsis thaliana* ecotype Columbia (Col-0) was received from Dr. Robert Sharrock, Montana State University. Following *Arabidopsis thaliana* mutants were obtained from the TAIR stock center and had a Col-0 background: ein2-1 (TAIR CS3071, ethylene insensitive), jar1-1 (TAIR CS8072, jasmonate resistance), ndr1-1/npr1-2 (TAIR CS6355, nonexpresser of PR genes and salicylic acid insensitive), and npr1-5 (TAIR CS3724, nonexpresser of PR genes and salicylic acid insensitive). The NahG mutant was obtained from Dr. Bob Dietrich, Syngenta, N.C.

Chemical Inducers:

Acibenzolar-s-methyl (ASM) (Actigard 50WG Fungicide, Syngenta, Greensboro, N.C.) as used as the chemical inducer for Col-O and NahG plants at a rate of 50 ug/ml of sterile distilled water. Probenazole (PBZ) (Chem Service, West Chester, Pa.) was used for npr1-5 mutants at a rate of 2 mM PBZ suspended in 0.1 M potassium phosphate buffer with 0.01% trition X-I 00. jar1-1 plants were treated with methyl jasmonate (Meta) (TCI America, Portland, Oreg.) at a rate of 7.5 mM in 0.8% ethanol. 1 mM of 2-chloroethylphosphonic acid (Ethephon, Acros Organics, NJ) dissolved in sterile-distilled water was the chemical inducer for ein2-1. All chemical inducers were applied using an aerosol sprayer with applications made to run-off.

Plant Culture, Treatments, Inoculation and Data Analysis.

Arahidopsis seeds were sown in flats containing Sunshine #1 mix (Sun Gro Horticulture Inc., Bellevue, Wash.) and vernalized for 4 days at 5±2° C. under 80% relative humidity (rh). They were then transferred to a growth chamber, sub-irrigated and kept at 22±2° C. day and 20 2° C. night temperature with a 10 hr photoperiod. After 3 weeks, individual plants were transplanted into plastic pots filled with Sunshine #1 mix supplemented with Osmocote Classic 14-14-14 (The Scotts Company, Marysville, Ohio) at a rate of 1.5 kg/m3 of Sunshine #1 mix. After 3 weeks, plants were induced either with distilled water, buffer, 203-7, BmJ, or the mutant specific chemical inducer by spraying the whole plant. After 6 days, plants were challenge inoculated with Bot-1 conidia solution by placing one 5 μl droplet on 3 individual leaves per plant. Following inoculation, plants were placed at conditions as described above and under 90% rh for 7 days to allow disease development. Disease severity was rated at a 0 to 5 scale with 0=no visible lesion to 5=lesion expanding into non-inoculated tissue. The experimental design was a randomized complete block with 20 replications per treatment for the *Botrytis cinerea*-bioassay and 8 replications per treatment for the PR-protein assays. Experiments were repeated three times. Data were analyzed statistically by conducting an analysis of variance using the general linear model procedure of the SAS program (SAS system, Version 9.00, SAS Institute Inc., Cary, N.C.). The treatment means were separated using Fisher's protected least significant difference test at P=0.05.

Apoplastic Fluid Extraction and Protein Quantification:

Apoplastic fluids were done as described by Klement, 1965. Protein amount of apoplastic fluids was quantified using Bio-Rad protein assay kit (Bio-Rad, Hercules, Calif.) per manufacturer's instructions using bovine serum albumin (EMD Chemicals Inc., Darmstadt, Germany) as standards.

Chitinase, p-glucanase and Superoxide Dismutase Assays:

Chitinase activity in apoplastic fluids was assayed as described by Hung et al. (2002). The microplate-based carboxymethylcellulose assay described by Xiao et al. (2005) was adapted to determine β-glucanase activity in apoplastic fluids. Quantification of superoxide dismutase (SOD) activity in the apoplastic fluid samples was performed according to the method described by Ewing and Janero (1995).

Results and Discussion:

Effects of the two BCAs and chemical inducers on disease reduction are shown in Table I. For all tested *Arabidopsis* lines (Col-O and mutants), the bacilli treatments and the chemical inducers were always significantly different (P=0.05) to the control plants treated with distilled water except for BmJ in ein2-1 mutants. Plants treated with the buffer controls alone were also significantly different to the control plants but had overall the lowest disease reduction when compared to the other treatments. Col-0 plants treated with BmJ were not significantly different (P=0.05) from plants treated with Actigard or 203-7. Plants treated with 203-7 showed a significant (P=0.05) disease reduction in npr1-1, NahG, and ein2-1 mutants when compared to the specific chemical inducers, but were not significantly different to PBZ in the ndr1-1/npr1-2 mutant or to BmJ treated NahG mutants. Jar1-1 mutants treated with either 203-7 or BmJ showed the lowest (P=0.05) disease reduction when compared to methyl jasmonate and were never significantly different (P=0.05) to each other or to plants treated with buffer. Applications with BmJ resulted in the lowest (P=0.05) disease reduction in ein2-1 mutants and in a decreased disease reduction similar (P=0.05) to buffer in npr1-5 mutants. These results confirm the work done in sugar beet (Bargabus-Larson and Jacobsen, 2007) that induction by BmJ is salicylic acid independent and both NPR1 dependent. Further it demonstrates that BmJ induction involves jasmonic acid/ethylene signaling. It also demonstrates that induction by 203-7 is jasmonic acid signaling dependent and NPR1 independent.

TABLE 6

Percent disease reduction of *Botrytis cinerea* leaf spot on *Arabidopsis thaliana* Col-O and Col-O mutants by means of induced SAR resulting from foliar applications of *Bacillus mojavensis* isolate 203-7, *B. mycoides* isolate BmJ or chemical inducer.

| Mutant Treatment | % disease reduction in comparison to distilled water | | | | |
|---|---|---|---|---|---|
|  | Col-0 | npr-5 | jar1-1 | NahG | ein2-1 |
| 203-7 | 38.4 B$^a$ | 52.4 d | 13.0 bc | 49.5 c | 36.8 c |
| BmJ | 41.3 bc | 9.9 b | 15.0 c | 49.5 c | 4.2 a |
| chemical inducer | 45.9 C (Actigard) | 41.9 c (PBZ) | 49.9 d (methyl jasmonate) | 32.6 b (Actigard) | 28.1 b (ethephon) |
| buffer | na | 7.9 b | 10.2 bc | na | na |
| distilled water | 0 a | 0 a | 0 a | 0 a | 0 a |

$^a$means in the same column followed by the same letter are not significant different according to Fisher's protected LSD (P = 0.05).

Wild type plants induced with BmJ and 203-7 had increased levels of chitinase (P=0.05) when compared to water controls while on ein2-1 mutants BmJ treatment did not increase chitinase levels. Chitinase levels in 203-7 induced wild type plants were equivalent to those induced with ASM but were not increased in jar1-1 mutants (P=0.05). BmJ did not increase p-glucanase activity in either wild type or mutant plants while 203-7 increased p-glucanase in wild type, npr1-5, NahG and ein2-1 mutants but not jar1-1 mutants (P=0.05). Both BmJ and 203-7 increased SOD activity in wild type plants (P=0.05). BmJ treatment did not increase SOD activity in npr1-5 or ein2-1 mutants. 203-7 induction resulted in increased levels of SOD in npr1-5, NahG and ein2-1 mutants (P=0.05). These results demonstrate that PR and SOD activity are induced where jasmonic acid signaling is required by 203-7 and that ethylene signaling is involved in PR and SOD activity increases in plants induced by BmJ. These results also demonstrate that our current classifications of SAR and ISR do not work for BmJ or 203-7 BCAs and that there is considerable crosstalk occurring between plant defense signaling systems in plants.

Example 15

Evaluation of Control on *Fusarium* Crown Rot by Induction of Systemic Acquired Resistance by *Bacillus mycoides* Isolate J and Acbenzolar-S-methyl Ester in Five Spring Wheat Cultivars Preparation of Plant Material The spring wheat cultivars Utopia (*Triticum durum*), Hank, Volt, MT0550, and Knudsen were used. Previously to seeding, the seeds were disinfected for 1 min with 10% sodium hypochloride and rinsed twice with sterile distilled water. Seeds were air dried for 3 hours in a fume hood. Pots (10 cm) with a capacity of 400 g of pasteurized MSU soil mix were used and four seeds were placed equidistant and at 2.0 cm of deep.

Inoculation Procedure.

Pots were inoculated 15 days post planting (dpp) with macroconidia of *Fusarium culmorum* isolate 2279 using a perforated microcentrifuge tube inserted in the center of the pot soil and equidistant of the emerged plants (FIG. 2). The soil inoculation was done by applying a suspension of spores of 1.0×106 macroconidia suspended in 20 mL of distilled water with a pipette. Macroconidia were obtained by growing fungus in Mung bean media for 10 days. The media was filtered through cheese cloth and the number of macroconidia was determined by counting using a hemacytometer.

Application of Inducers.

Cultivars were sprayed with both inducers and a water control. Defenses were chemically activated by spraying plants with four leaves 3 days before inoculation. A suspension of ddH20 with 0.01% Tween 20 containing BmJ at $1.5\times10^8$ CFU per ml, 1.0 mM ASM (commercial formulation Actigard, Syngenta) solution, or only water were sprayed on the cultivars. All plants were sprayed until runoff (−1.7 mL per plant) and maintained separated inside of the glasshouse by 2 h until foliage were dry. Sprayings were repeated at 19, 26 and 33 days post planting. Plants were grown until Feekes stage 11 and during this time pots were maintained on trays and watered by infiltration each two days with 4 liters of water per 18 pots. Fertilizer was applied weekly as needed.

Disease Assessment

Treatments were randomized on each cultivar. FCR severity was determined by using a crown rot rating (CRR) scale of 1 to 4 on the first internode of each plant, whereby: 1=0-5%; 2=5-50%; 3=50-85%; and 4=85-100% internode discoloration. A disease severity index (DSI) was determined by summing the individual CRRs and dividing this for the possible maximum value of infection and multiplying by 100 to create a DSI percentage for each pot.

Data Analysis

Each SAR inducer treatment was assessed individually with a randomized design and inducer treatments and cultivars were considered as factors in a factorial analysis. ANOVA were performed by the SAS procedure, Proc GLM (Version 8.0, Inc. Cary, N.C., USA). Least significant difference (LSD) range test was used to compare means ($\alpha$<0.05).

Results

The results are shown in Table 7. Analysis of the level of control of the biological and chemical inducers showed statistical differences for disease severity for cultivar (P=0.0003) and for treatment (P=0.03) but no cultivar×treatment interactions (P=0.17) were detected. Over all treatments, the cultivars Knudsen and Volt were less susceptible than Utopia and MT 0550 while Hank was more susceptible than Volt but equivalent to Knudsen (P=0.0003). Knudsen and Volt are *Fusarium* head blight (FHB) resistant cultivars, and the resistance to FHB has been associated with the induction of different PR-proteins (Pritsch, et al., 2000). Knudsen is a cultivar derived from the FHB resistant genome Sumai 3, which has showed that chitinases and β-1,3-glucanases are accumulated faster (Pritsch, et al., 2000). Analysis for each cultivar showed BmJ reduced FCR severity only on the most resistant cultivar, Volt (P=0.05). These results suggest the potential to use BmJ with cultivar resistance for control of FCR, which could be improved if this inducer is incorporated to an Integrated Pest Management with a fungicide seed treatment. ASM reduced FCR severity only on MT 0550 (P=0.02), but over all cultivars, ASM reduced FCR severity significantly from the water control while BmJ was intermediate (P=0.03).

TABLE 7

Control on Fusarium crown rot by *Bacillus mycoides* Isolate J and Acbenzolar-S-methyl ester in five spring wheat cultivars

| Treatments | Cultivars Disease Severity Index (%) | | | | | |
|---|---|---|---|---|---|---|
| | Utopia | Knudsen | MT 0550 | Hank | Volt | Average |
| Control | 67.38 | 47.95 | 69.47 a | 54.88 | 50.02 a | 57.94 a |
| BmJ | 55.92 | 49.33 | 71.88 a | 51.07 | 33.70 b | 52.38 ab |
| ASM | 60.43 | 46.88 | 42.73 b | 48.97 | 37.53 ab | 47.31 b |
| Average | 61.24 a | 48.06 bc | 61.36 a | 51.64 ab | 40.42 c | P Trt = 0.0325 |
| P-value | 0.5647 | 0.966 | 0.022 | 0.7021 | 0.0506 | P cvs = 0.0003 |
| of e/cvs. | | | Interaction Cvs × Trt P-value = | | | 0.1703 |

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. F B Abeles, R P Bosshart, L E Forrence and W H Habig, Preparation and purification of glucanase and chitinase from bean leaves. Plant Physiology 47 (1970), pp. 129-134.
2. S Alstrom, Induction of disease resistance in common bean susceptible to halo blight bacterial pathogen after seed bacterisation with rhizosphere pseudomonads. Journal of Genetic and Applied Microbiology 37 (1991), pp. 495-501.
3. A J Anderson, Studies on the structure and elicitor activity of fungal glucans. Canadian Journal of Botany 58 (1980), pp. 2343-2348.
4. J H Andrews, Biological control in the phyllosphere. Annual Review of Phytopathology 30 (1992), pp. 603-635.
5. A Braun-Kiewnick, S Kiewnick and B J Jacobsen, Induction of systemic resistance by antagonistic *Bacillus* sp. and the chemical inducer benzothiadiazole controls *Cercospora* leaf spot of sugar beet. Phytopathology 88 (1998), p. S10.
6. W M Bugbee, *Cercospora beticola* tolerant to triphenyltin hydroxide. Journal of Sugar Beet Research 32 (1995), pp. 51-79.
7. J M Chittoor, E Leach and F F White, Induction of peroxidase during defense against pathogens. In: A A Agrawal, S Tuzun and E Bent, Editors, Induced Plant Defenses Against Pathogens and Herbivores, APS Press, St Paul (1999), pp. 171-193.
8. Y Cohen, M Reuveni and A Baider, Local and systemic activity of BABA (DL-3-aminobutyric acid) against *Plasmopara viticola* in grapevines. European Journal of Plant Pathology 105 (1999), pp. 351-361.
9. Y R Cohen, β-aminobutyric acid-induced resistance against plant pathogens. Plant Disease 86 (2002), pp. 448-457.
10. T P Delaney, Genetic dissection of acquired resistance to disease. Plant Physiology 113 (1997), pp. 5-12.
11. N Doke, Generation of superoxide anion by potato tuber protoplasts during the hypersensitive response to hyphal wall components of *Phytophthora infestans* and specific inhibition of the reaction by suppressors of hypersensitivity. Physiological Plant Pathology 23 (1983), pp. 359-367
12. J E Duffus and E G Ruppel, Diseases. In: D A Cooke and R K Scott, Editors, Diseases in the Sugarbeet Crop, Chapman and Hall, London (1993), pp. 346-427.
13. S Gallagher, S E Winston, A Fuller and J G R Hurrell, Immunoblotting and Immunodetection. In: F M Ausubel, R Brent, R E Kingston, D D Moore, J G Seidman, J A Smith and K Stall* Editors, Current Protocols in Molecular Biology, John Wiley and Sons, Inc, New York (1997), pp. 10.8.1-10.8.16.
14. T E Gottschalk, J D Mikkelsen, K K Nielsen and J Brunstedt, Immunolocalization and characterization of a (β-1, 3-glucanase from sugar beet, deduction of its primary structure and nucleotide sequence by cDNA and genomic cloning. Plant Science 132 (1998), pp. 153-167.
15. R Hammerschmidt, E M Nuckles and J Kuc, Association of enhanced peroxidase activity with induced resistance of cucumber to *Colletotrichum lagenarium*. Physiological Plant Pathology 20 (1982), pp. 73-82.
16. R Hofstein and A Chapple, Commercial development of biofungicides. In: F R Hall and J J Menn, Editors, Biopesticides: Use and Delivery, Humana Press, Totowa (1999), pp. 77-102.

17. S W Hutcheson, Current concepts of active defense in plants. Annual Review of Phytopathology 36 (1998), pp. 59-90.
18. B J Jacobsen, N K Zidack, J Ansley, B Larson, J LA Eckhoff and J Bergman, Integrated management of cercospora leaf spot. Sugarbeet Research and Extension Reports 32 (2001), pp. 317-320.
19. E Jongedijk, H Tigelaar, J SC van Roekel, S A Bres-Vloemans, I Dekker, P J M van den Elzen, B J C Cornelissen and L S Melchers, Synergistic activity of chitinases and (β-1,3-glucanases enhances fungal resistance in transgenic tomato plants. Euphytica 85 (1995), pp. 173-180.
20. Kleinwanzler Saatzucht, Ag, Einbeck, 1970, *Cercospora* Tafel. Kleinwanzleber Saatzacht Ag, 14 p
21. K Klement, Method of obtaining fluid from the intercellular spaces of foliage and the fluid's merit as substrate for phytobacterial pathogens. Phytopathology 55 (1965), pp. 1033-1034.
22. N Kokalis-Burelle, P A Backman, R Rodriquez-Kabana and L D Ploper, Potential for biological control of early leafspot of peanut using *Bacillus cereus* and chitin as foliar amendments. Biological Control 2 (1992), pp. 321-328.
23. J Kuc, Induced immunity to plant disease. BioScience 32 (1992), pp. 854-860.
24. M Legrand, S Kauffmannn, P Geoffroy and B Fritig, Biological function of pathogenesis-related proteins: four tobacco pathogenesis-related proteins are chitinases. Proceedings of the National Academy of the Sciences, USA 84 (1987), pp. 6750-6754.
25. T Lotan, N On and R Fluhr, Pathogenesis-related proteins are developmentally regulated in tobacco flowers. The Plant Cell 1 (1989), pp. 881-887.
26. T Maniatis, E F Fritsch and J. Sambrock. Molecular Cloning: A Laboratory Manual, Cold Spring Harbor Laboratory, Cold Spring Harbor (1982) p. 18.56-18.57.
27. F Mauch, B Mauch-Mani and T Boller, Antifungal hydrolases in pea tissue. Plant Physiology 88 (1988), pp. 936-942.
28. J-P Metraux and T h Boller, Local and systemic induction of chitinase in cucumber plants in response to viral, bacterial and fungal infections. Physiological and Molecular Plant Pathology 28 (1986), pp. 161-169.
29. J-P Metraux, P Ahl-Goy, T Staub, J Speich, A Steinemann, J Ryals and E Ward, Induced resistance in cucumber in response to 2,6-dichloroisonicotinic acid and pathogens. In: H Hennecke and D P S Verma, Editors, Advances in Molecular Genetics of Plant-Microbe Interactions, Vol. 1, Kluwer Academic Publishers, Dordrecht (1991), pp. 432-439.
30. B M Moerschbacher, Plant peroxidases: involvement in response to pathogens. In: C Penel, T h Gaspar and H Greppin, Editors, Plant Peroxidases 1980-1990, Topics and Detailed Literature on Molecular, Biochemical and Physiological Aspects, University of Geneva Press, Geneva (1992), pp. 91-99.
31. J F Murphy, G W Zehnder, D J Schuster, E J Sikora, J E Polston and J W Kloepper, Plant growth-promoting rhizobacterial mediated protection in tomato against Tomato mottle virus. Plant Disease 84 (2000), pp. 779-784.
32. A Navarro, P Manzanares, J V Carbonell and J M Sendra, Determination of (1 leads to 3), (1 leads to 4)-β-glucanase activity by a Calcofluor-flow injection analysis method. Journal of Cereal Science 22 (1995), pp. 275-284.
33. N Nelson, A photometric adaptation of the Somogyi method for the determination of glucose. Journal of Biological Chemistry 153 (1994), pp. 375-380.
34. J M Neuhaus, S Flores, D Keefe, P Ahl-Goy and F Meins, Jr., The function of vacuolar β-1,3-glucanase investigated by antisense transformation. Susceptibility of transgenic *Nicotiana sylvestris* plants to *Cercospora nicotianae* infection. Plant Molecular Biology 19 (1992), pp. 803-813.
35. Y Oka, Y Cohen and Y Spiegel, Local and systemic induced resistance to the root-knot nematode in tomato by DL-β-amino-n-butyric acid. Phytopathology 89 (1999), pp. 1138-1143.
36. C M J Pieterse, S CM van Wees, E Hoffland, J A van Pelt and L C van Loon, Systemic resistance in *Arabidopsis* induced by biocontrol bacteria is independent of salicylic acid accumulation and pathogenesis-related gene expression. The Plant Cell 8 (1996), pp. 1225-1237.
37. C M J Pieterse, S CM van Wees, J A van Pelt, M Knoester, R Laan, H Gerrits, P J Weisbeek and L C van Loon, A novel signaling pathway controlling induced systemic resistance in *arabidopsis*. The Plant Cell 10 (1998), pp. 1571-1580.
38. Z K Punja, Genetic engineering of plants to enhance resistance to fungal pathogens a review of progress and future prospects. Canadian Journal of Plant Pathology 23 (2001), pp. 216-235.
39. R A Reisfeld, U J Lewis and D E Williams, Disk electrophoresis of basic proteins and peptides on polyacrylamide gels. Nature 195 (1962), pp. 281-283.
40. A F Ross, Localized acquired resistance to plant virus infection in hypersensitive hosts. Virology 14 (1961a), pp. 329-339.
41. A F Ross, Systemic acquired resistance induced by localized virus infection in plants. Virology 14 (1961b), pp. 340-358.
42. J A Ryals, U H Neuenschwander, M G Willits, A Molina, H Y Steiner and M D Hunt, Systemic acquired resistance. The Plant Cell 8 (1996), pp. 1809-1819.
43. L Sequeira, Mechanisms of induced resistance in plants. Annual Review of Microbiology 37 (1983), pp. 51-79.
44. K P Smith, J Handelsman and R M Goodman, Modeling dose-response relationships in biological control: partitioning host responses to the pathogen and biocontrol agent. Phytopathology 87 (1997), pp. 720-729.
45. M Somogyi, Notes on sugar determination. Journal of Biological Chemistry 195 (1952), pp. 19-23.
46. J P Stack, Biological management of postharvest diseases. Phytopathology 92 (2002), p. S106.
47. J C Sutton and G Peng, Manipulation and vectoring of biocontrol organisms to manage foliage and fruit diseases in cropping systems. Annual Review of Phytopathology 31 (1993), pp. 473-493.
48. A Tally, M Oostendorp, K Lawton, T Staub and B Bassi, Commercial development of elicitors of induced resistance to pathogens. In: A A Agrawal, S Tuzun and E Bent, Editors, Induced Plant Defenses Against Pathogens and Herbivores, APS Press, St Paul (1999), pp. 299-318.
49. S Thamthiankul, S Suan-Ngay, S Tantimavanich and W Panbangred, Chitinase from *Bacillus thurigiensis* subsp. *Pakistani*. Applied Microbiology and Biotechnology 56 (2001), pp. 395-401.
50. J Trudel and A Asselin, Detection of chitinase activity after polyacrylamide gel electrophoresis. Analytical Biochemistry 178 (1989), pp. 362-366.
51. L C van Loon, Occurrence and properties of plant pathogenesis-related proteins. In: A A Agrawal, S Tuzun and S Bent, Editors, Induced Plant Defenses Against Pathogens and Herbivores, APS Press, St Paul (1999), pp. 1-19.
52. L C van Loon and E A van Strien, The families of pathogenesis-related proteins, their activities, and comparative analysis of PR-1 type proteins. Physiological and Molecular Plant Pathology 55 (1999), pp. 85-97.
53. L C van Loon and C M J Pieterse, Biological control agents in signaling resistance. In: S S Gnanamanickan, Editor, Biological Control of Crop Diseases, Mercel Dekker, New York (2002), pp. 355-386.
54. R van Peer, G J Niemann and B Schippers, Induced resistance and phytoalexin accumulation in biological control of *fusarium* wilt of carnation by *Pseudomonasa* sp. strain WCS417r. Phytopathology 81 (1991), pp. 728-734.
55. L Velasquez. The Pathogenesis-related Protein Chitinase, and its Role in the Systemic Acquired Resistance Phenotype in Cucumber Plants (*Cucumis sativus* L.), Michigan State University (2002) p. 25-49.
56. G Wei, J W Kloepper and S Tuzun, Induction of systemic resistance of cucumber to *Colletotrichum orbiculare* by select strains of plant growth-promoting rhizobacteria. Phytopathology 81 (1991), pp. 1508-1512. Full Text via CrossRef
57. D M Weller, Biological control of soil-borne plant pathogens in the rhizosphere with bacteria. Annual Review of Phytopathology 26 (1988), pp. 379-407.
58. R F White, Acetylsalicylic acid (aspirin) induces resistance to tobacco mosaic virus in tobacco. Virology 99 (1979), pp. 410-412.
59. C E Windels, H A Lamey, D Hilde, J Widner and T Knudsen, A *Cercospora* leaf spot model for sugar beet: In practice by an industry. Plant Disease 82 (1998), pp. 716-726. Full Text via CrossRef|View Record in Scopus|Cited By in Scopus (28)
60. S Zhang, M S Reddy, N Kokalis-Burelle, L W Wells, S P Nightengale and J W Kloepper, Lack of induced systemic resistance in peanut to late leaf spot disease by plant growth-promoting rhizobacteria and chemical elicitors. Plant Disease 85 (2001), pp. 879-884. Full Text via CrossRef|View Record in Scopus|Cited By in Scopus (13)
61. Q Zu, A Maher, S Masoud, R A Dixon and C Lamb, Enhanced protection against fungal attack by constitutive coexpression of chitinase and glucanase genes in transgenic tobacco. Bio Technology 12 (1994), pp. 807-812.
62. Bargabus, R. L., Zidack, N. K., Sherwood, J. E., Jacobsen, B J., 2003. Characterization of systemic resistance in sugar beet elicited by a non-pathogenic, phyllosphere-colonizing *Bacillus mycoides*, biological control agent. Physiological and molecular plant pathology 61: 289-298.
63. Bargabus, R. L., Zidack, N. K, Sherwood, I E., Jacobsen, B J., 2004. Screening for the identification of potential biological control agents that induce systemic acquired resistance in sugar beet. Biological Control 30: 342-350.
64. Bargabus-Larson, R. L. and B J. Jacobsen, 2007. Biocontrol elicited systemic resistance in sugarbeet is salicylic acid independent and npr1 dependent 1 Sugar Beet Res. 44: 17-33.
65. Ewing, J. F., Janero, D. R., 1995. Microplate superoxide dismutase assay employing a nonenzymatic superoxide generator. Analytical Biochemistry 232: 243-248.
66. Hung, T.-H., Chang, Y.-M., Sung, H.-Y., Chang, C.-T., 2002. Purification and Characterization of hydrolase with chitinase and chitosanase activity from commercial stem bromelain. Journal of Agricultural and Food Chemistry 50: 4666-4673.
67. Jacobsen, B. l. 2006. Biological control of plant diseases by phyllosphere applied biological control agents. p. 133-148, In: Microbial Ecology of Aerial Plant Surfaces, (Ed) M. Baily et al. CAB International, Cambridge, Mass. 315 p.
68. Jacobsen, B. l., C. Bradley, N. Zidack, T. Brenneman, I Miller, I Washington, C. Melinger, B. Larson and a. Neher. 2007. Commercialization of *Bacillus mycoides* isolate BmJ as a broad spectrum biological plant disease control agent. Phytopathology 97: S50
69. Pieterse, C. M. l., van Wees, S. C. M., van Pelt, I A, Knoester, M., Laan, R., Gerrits, H., Weisbeek, P. l., van Loon, L.c., 1998. A novel signaling pathway controlling induced systemic resistance in *Arabidopsis*. Plant Cell 10: 1571-1580.
70. Verhagen, B. W. M., van Loon, L.c., Pieterse, C. M. l., 2006. Induced disease resistance in plants. pp 334-343. In: Floriculture, ornamental and plant biotechnology, (Ed) Teixeira da Silva, IA Global Science Books ltd, UK.
71. Xiao, Z. Z., Storms, R., Tsang, A, 2005. Microplate-based carboxymethylcellulose assay for endoglucanase activity. Analytical Biochemistry 342: 176-178.
72. Zietlow, a. T., M. R. Johnston, N. K. Zidack and B. l. Jacobsen. 2004. Induced systemic resistance in cucumber to *Glomerella cingulata* var. *obiculare* and *Pseudomonas syringae* pv. *lachrymans* by *Bacillus pumilis*, isolate MSU 203-7. Phytopathology 94: S117.

We claim:

1. An isolated *Bacillus* strain, wherein the isolated strain is *Bacillus mycoides* isolate J (BmJ) deposited under accession number NRRL B-30890.

2. An isolated *Bacillus* strain having all of the physiological and morphological characteristics of *Bacillus mycoides* isolate J (BmJ) deposited under accession number NRRL B-30890.

3. Progeny of the isolated *Bacillus* strain of claim 1, wherein inoculating a host plant or a part of said plant with a culture of said progeny induces disease resistance in the plant or the plant part.

4. The isolated strain of claim 1, wherein the strain or progeny is isolated from a plant, or a plant part.

5. The isolated strain of claim 4, wherein the plant is a dicot plant or said plant part is from a dicot plant.

6. The isolate strain of claim 5, wherein the dicot plant is a sugar beet plant.

7. The isolated strain of claim 4, wherein the plant part is a plant leaf.

8. The progeny of claim 3, wherein the disease resistance is salicylic acid independent.

9. The isolated strain of claim 1, wherein the strain is in endospore form.

10. An isolated *Bacillus* cell, wherein the isolated cell is derived from the *Bacillus mycoides* isolate J (BmJ) deposited under accession number NRRL B-30890.

11. The isolated *Bacillus* cell of claim 10, wherein inoculating a host plant or a part of said plant with a composition comprising said cell induces disease resistance in the plant or the plant part.

12. The isolated *Bacillus* cell of claim 11, wherein the disease resistance is salicylic acid independent.

13. A composition comprising the isolated *Bacillus* strain of claim 1, or the isolated *Bacillus* cell of claim 10.

14. The composition of claim 13, wherein the composition is in a spray-dried formulation.

15. The composition of claim 14, wherein the spray-dried formulation is suspended in water before inoculation to a plant or a plant part.

16. The composition of claim 13, wherein the composition comprising at least $1 \times 10^7$ cfu/ml BmJ.

* * * * *